United States Patent [19]

McCabe et al.

[11] Patent Number: 5,576,436

[45] Date of Patent: Nov. 19, 1996

[54] FLUORESCENT LIGANDS

[75] Inventors: R. Tyler McCabe, South Salem, N.Y.; Christopher A. Rhodes, Stamford, Conn.; Bruce F. DeCosta, Yonkers, N.Y.

[73] Assignee: Pharmaceutical Discovery Corporation, Elmsford, N.Y.

[21] Appl. No.: 204,559

[22] Filed: Mar. 2, 1994

Related U.S. Application Data

[63] Continuation-in-part of Ser. No. 923,837, Jul. 31, 1992, abandoned, which is a continuation-in-part of Ser. No. 739,183, Aug. 1, 1991, abandoned.

[51] Int. Cl.$^6$ .................................................. C07D 271/12
[52] U.S. Cl. ...................... 546/156; 548/126; 549/227; 549/283; 554/43; 564/86
[58] Field of Search ........................... 548/126; 549/227, 549/283; 564/86; 554/43; 546/156

[56] References Cited

U.S. PATENT DOCUMENTS

| | | | |
|---|---|---|---|
| 4,784,961 | 11/1988 | Russell | 436/63 |
| 5,280,015 | 1/1994 | Jacobsen et al. | 514/46 |

FOREIGN PATENT DOCUMENTS

| | | |
|---|---|---|
| 0126612 | 11/1984 | European Pat. Off. |
| WO93/03382 | 10/1993 | WIPO |

OTHER PUBLICATIONS

Ariano, M. A., et al., "Direct visualization and cellular localization of $D_1$ and $D_2$ dopamine receptors in rat forebrain by use of fluroescent ligands," *Proc. Natl. Acad. Sci. U.S.A.*, 86:8570–8 8574 (Nov. 1989).

Atlas, D., Levitzki, A., "Probing of β–adrenergic receptors by novel fluorescent β–adrenergic blockers," *Proc. Natl. Acad. Sci. USA*, 74:5490–65294 (1977).

Barnes, P., et al., "A fluorescent analogue of propranolol does not label beta adrenoceptor sites," *Brain Res.*, 181:209–213 (1980).

Carlson, K. E., et al., "Receptor Binding of NBD–labeled Fluorescent Estrogens and Progestins in Whole Cells and Cell–free Preparations," *J. Steroid Biochem.*, 32:345–355 (1988).

Cohen, V. I., et al., "Synthesis and Structure–Activity Relationship of Some 5–[[[(Dialkylamino)alkyl]–1–piperidinyl] acetyl]–10,11–dihydro–5H–benzo[b,e][1,4] diazepin–11–ones as $M_2$ Selective Antimuscarinics," *J. Med. Chem.*, 36:162–165 (1993).

Correa, F. M. A., et al., "Fluorescent Probes and β–Adrenergic and Opiate Receptors: Biochemical nad Histochemical Evaluation," *Neurosci. Lett.*, 15:47–53 (1980).

Havuniian, R. H., et al., "Characterization of Benzodiazepine Receptors with a Fluorescence–quenching Ligand," *J. Biol. Chem.*, 265(36):22181–22186 (Dec. 25, 1990).

Heithier, H., et al., "Fluorescent glucagon derivatives, I. Synthesis and characterisation of fluorescent glucagon derivatives," *Biochim. Biophys. Acta*, 971:298–306 (1988).

Henis, Y., I., et al., "Lateral motion of β receptors in membranes of cultured liver cells," *Proc. Natl. Acad. Sci. USA* 79:2907–2911 (1982).

Hess, A., "Visualization of beta–adrenergic receptor sites with fluorescent beta–adrenergic blocker probes–or autofluorescent granules?," *Brain Res.*, 160:533–538 (1979).

Jacobson, K. A., et al., "Molecular probes for extracellular adenosine receptors," *Biochemical Pharmacology*, 36(10):1697–1707 (1987).

Johansson, B., et al., "The Binding of the Adenosine $A_2$ Receptor Selective Against [$^3$H]CGS 21680 to Rat Cortex Differs From Its Binding to Rat Striatum," *Eur. J. Pharmacology–Molecular Pharmacology Sec.*, 247:103–110 (1993).

Kolb, V. M. et al., "Fluorescent Probes for Opioid Receptors," *Life Sci.*, 33:423–426 (1983).

McCabe, T., et al., "Characterization of Benzodiazepine Receptors with Fluorescent Ligands," *FASEB Journal*, 4:2934–2936 (1990).

McCabe, R. T., et al., "Characterization of [$^3$H]Alprazolam Binding to Central Benzodiazepin Receptors," *Pharmacology Biochem. Behavior*, 37:365–370, (May 1990).

McCabe, R. T., et al., "2–[2–[4–[2–[2–[1,3–Dihydro–1, 1–bis(4–hydroxyphenyl)–3–oxo–5– isobenzofuranthioureidyl]ethylaminocarbonyl]phenyl] ethylamino]–5′–N–ethylcarboxamidoadenosine (FITC–APEC): A Fluorescent Ligand for $A_{2a}$–Adenosine Receptors," *J. Fluorescence*, 2(4):217–223 (1992).

McCabe, R. T., et al., "AHN 683: A Fluorescent Ligand for Peripheral–Type Benzodiazepine Receptors," *J. Pharmacology and Experimental Therapeutics*, 262(2):734–740 (1992).

Monsma, F. J., Jr., et al., "Characterization of Novel Fluorescent Ligands with High Affinity for $D_1$ and $D_2$ Dopaminergic Receptors," *J. Neurochem.*, 52(5)1641–1644 (1989).

Olsen, R. W., et al., "$GABA_A$ Receptor Subtypes: Autoradiographic Comparison of GABA, Benzodiazepine, and Covulsant Binding Sites in the Rat Central Nervous System," *J. Chem. Neuroanatomy*, 3:59–76(Jan. 1990).

Pascali, C., et al., "the Radiosynthesis of [18F]PK 14105 as an Alternative Radioligand for Peripheral Type Benzodiazepine Binding Sites," *App. Radiat. Isot.*, 41(5):477–482 (1990).

Rademaker, B., et al., "Irreversible Binding of the Fluorescent Beta–Adrenoceptor Probes Alprenolol–NBD and Pindolol–NBD to Specific and Non–specific Binding Sites," *Res. Commun. Chem. Pathol. Pharmacol.*, 60:147–159 (1988).

Rademaker, B., et al., "High Affinity Non–β–Adrenoceptic Binding of β–Adrenergic Ligands" *Eur. J. Pharmacol.*, 111:31–36 (1985).

(List continued on next page.)

*Primary Examiner*—Richard L. Raymond
*Attorney, Agent, or Firm*—Arnall Golden & Gregory

[57] ABSTRACT

Conjugates of fluorescent labels with specific, selective, and high affinity ligands for receptors have been synthesized and used to directly measure binding to receptors.

10 Claims, No Drawings

OTHER PUBLICATIONS

Rademaker, B., et al., "Non-specific Binding of the Fluorescent β–Adrenergic Receptor Probe Alprenolol–NBD," *J. Receptor Res.*, 5:121–131 (1985).

Snyder, S. H., "Drug and Neurotransmitter Receptors, New Perspective with Clinical Relevance," *J. Am Med. Assoc.*, 261:3126–3129 (1989).

Velasquez., J. L., et al., "Distrubution and Lateral Mobility of GABA/Benzodiazepine Receptors on Nerve Cells," *J. Neuroscience*, 9(6):2163–2169 (Jun. 1989).

Ward, L., et al. "Fluorescent glucagon derivatives II. The use of fluorescent glucagon derivatives for the study of receptor disposition in membranes," *Biochim. Biophys. Acta*, 971:298–306 (1988).

Yamamura, H.. I., eds., *Neurotransmitter Receptor Binding*, 2nd ed. (Raven Press, New York, 1988).

Toyooka et al, Chemical Abstracts, vol. 115 (1991) 84549.

Bergbreiter et al, Chemical Abstracts, vol. 112 (1990) 57277.

Albaugh et al, Chemical Abstracts, vol. 111 (1989) 243118.

Junker–Buchheit et al, Chemical Abstracts, vol. 111 (1989) 146031.

Junker–Buchheit et al., Chemical Abstracts, vol. 110 (1988) 127795.

Russell, Chemical Abstracts, vol. 107 (1987) 92959.

FLUORESCENT LIGANDS

The United States has rights in this invention by virtue of NIH Grants NS22071, NS21908, HD06576 and HD22702.

This is a continuation-in-part of U.S. patent Ser. No. 07/923,837, filed Jul. 31, 1992, by R. Tyler McCabe and Christopher A. Rhodes, now abandoned, which is a continuation-in-part of Ser. No. 07/739,183, filed Aug. 1, 1991, by R. Tyler McCabe, now abandoned.

BACKGROUND OF THE INVENTION

This invention is generally in the area of fluorescently labelled reagents for measuring binding reactions with specific cell receptors.

Radioligand binding techniques have been widely used for more than a decade to study receptor pharmacology and physiology. These methodologies provide a rapid, efficient means for drug discovery and identification of putative endogenous substances that may physiologically subserve receptors, as reviewed by Yamamura, H. I., Enna, S. J., and Kuhar, M. J., eds., in *Neurotransmitter Receptor Binding*, 2nd ed. (Raven Press, New York 1988) and Snyder, S. H. "Drug and neurotransmitter receptors. New perspectives with clinical relevance." *J. Am. Med. Assoc.* 261, 3126–3129 (1989). These studies are particularly useful in characterizing drug-receptor interactions and specificities.

For example, in *J. Chem. Neuroanatomy*, 3:59–76 (January 1990), Olsen, R. W., R. T. McCabe, and J. K. Wamsley, described the characterization of $GABA_A$ receptor subtypes using autoradiographic comparison of GABA, benzodiazepine, and convulsant binding sites in the rat central nervous system. The regional distribution of radioactive ligand binding in rat brain for the different receptors of the gammaaminobutyric $acid_A$ ($GABA_A$)-benzodiazepine receptor/Chloride channel complex was measured on tissue sections by autoradiography. Seven ligands were employed including [$^3$H]muscimol for high-affinity GABA agonist sites; [$^3$H]bicuculline methochloride and [$^3$H]SR-95531 for the low-affinity GABA sites; [$^3$H]flunitrazepam for benzodiazepine sites, and [$^3$H]2-oxo-quazepam for the 'BZ1'-type subpopulation; and [$^{35}$S]t-butyl bicyclophosphorothionate (TBPS) and [$^3$H]t-butyl bicyclo-orthobenzoate (TBCB) for convulsant sites associated with the chloride channel. Allosteric interactions of benzodiazepine receptor ligands with [$^{35}$S]TBPS binding were also examined in membrane homogenates. Comparison of 19 brain regions indicated areas of overlap between these ligands, but also significant lack of correspondence in some regions between any two ligands compared. Significant differences were observed in comparing GABA agonists with antagonists, one antagonist with another, GABA ligands with benzodiazepine or convulsant sites, and even between the two convulsants TBPS and TBOB. It is likely that the characterization of receptors as subtypes based on binding alone indicate a pharmacological heterogeneity that might be exploited with subtype-specific drugs showing desirable clinical profiles.

As described by R. T. McCabe, D. R. Mahan, R. B. Smith, and J. K. Wamsley in *Pharmacology Biochem. Behavior* 37: 365–370 (May 1990), the binding of the triazolobenzodiazepine [$^3$H]alprazolam was studied to characterize the in vitro interactions with benzodiazepine receptors in membrane preparations of rat brain. Alprazolam, an agent used as an anxiolytic and in the treatment of depression, acts in vitro as a selective and specific ligand for benzodiazepine receptors in the rat brain. Studies using nonequilibrium and equilibrium binding conditions for [$^3$H]prazolam resulted in high specific to nonspecific (signal to noise) binding ratios. The binding of [$^3$H]alprazolam was saturable and specific with a low nanomolar affinity for benzodiazepine receptors in the ran brain. GABA enhanced [$^3$H]alprazolam binding while several benzodiazepine receptor ligands were competitive inhibitors of this drug. Compounds that bound to other receptor sites had a very weak or negligible effect on [$^3$H]alprazolam binding.

Despite the usefulness and sensitivity of radioligand binding techniques, the use of alternative methods to study ligand-receptor interactions may provide information not readily accessible by conventional radioreceptor techniques and circumvent some of the drawbacks (such as high cost, disposal, and potential health hazard) associated with this methodology.

Fluorescence techniques have successfully been employed to study the behavior of ligand-protein interactions. For example, fluorescent labeled substrates and antigens have proven valuable in the examination of substrate-enzyme and antigen-antibody interactions.

Several attempts have been made to use fluorescent compounds to characterize receptors. Ligands with fluorescent moieties were prepared for α-adrenergic (Correa, F. M. A., et al., *Neurosci. Lett.* 16, 47–53 (1980)); β-adrenergic (Atlas, D., and Levitzki, A. *Proc. Natl. Acad. Sci. USA* 74, 5290–5294 (1977); Henis, Y. I., et al., *Proc. Natl. Acad. Sci. USA* 79, 2907–2911 (1982); and Rademaker, B., et al., *Res. Commun. Chem. Pathol. Pharmacol.* 60, 147–159 (1988)); opioid (Correa, et al., (1980) and Kolb, V. M., et al., *Life Sci.* 33, 423–426 (1983)); adenosine (Jacobson, K. A., et al., *Biochem. Pharmacol.* 36, 1697–1707 (1987)); glucagon (Heithier, H., et al., *Biochim. Biophys. Acta* 971, 298–306 (1988) and Ward, L. D., et al., *Biochim. Biophys. Acta* 971, 307–316 (1988)); steroid (Carlson, K. E., et al., *J. Steroid Biochem.* 32, 345–355 (1988)); and dopamine (Monsma, F. J., Jr., et al., *J. Neurochem.* 52, 1641–1644 (1989)) receptors.

Although many of the ligands with fluorescent moieties were reported to have moderate to high affinities when evaluated with radioligand assays, quantitation and visualization of ligand-receptor interactions by direct fluorescence measurement have been problematic. For example, investigations using fluorescent ligands to identify receptors were equivocal owing to high levels of tissue autofluorescence and apparent lack of specificity (Correa, F. M. A., et al., (1980), Rademaker, B., et al., (1988), (Hess, A. *Brain Res.* 160, 533–538 (1979); Barnes, P., et al., *Brain Res.* 181, 209–213 (1980); Rademaker, B., et al., *Eur. J. Pharmacol.* 111, 31–36 (1985); and Rademaker, B., et al., J. Recept. Res. 5, 121–131 (1985)). Carlson, et al. (1988) described an ethyl acetate extraction technique to analyze fluorescent ligands for steroid receptors. Nevertheless, direct quantitation of ligand-receptor interactions with fluorescent ligands has not been demonstrated conclusively.

It is therefore an object of the present invention to provide fluorescent ligands for use in directly quantitating ligand-receptor interactions.

It is a further object of the present invention to provide a method and reagents for use in determining ligand-receptor interactions intracellularly and extracellularly.

SUMMARY OF THE INVENTION

Fluorescent labeled ligands were prepared for use in receptor binding studies by covalently binding a ligand, such as a compound specifically and selectively binding to benzodiazepine, cannabinoid, glycine, muscarinic, opioid, N-methyl D-aspartate (NMDA), β- and α-adrenergic, dopamine or serotonin receptors, or potassium or sodium channel sites, to a fluorescent label, wherein the labeled ligand binds specifically to a receptor or ion channel site with an affinity of less than or equal to one micromolar and the label is directly detectable in the visible spectrum. The fluorescent labeled ligands are particularly useful in direct assays of binding intracellularly, as well as extracellularly, and in competitive binding studies to determine the specificity and affinity of uncharacterized compounds.

In the examples, fluorescent conjugates of kappa$_1$-opioid receptor ligands, N-methyl-D-aspartate receptor ligands, a glibenclamide receptor ligand, benzodiazepine receptor ligands, cannabinoid receptor ligands, dopamine$_1$ receptor ligand, dopamine$_2$ receptor ligand, muscarinic$_1$ receptor ligand, muscarinic$_2$ receptor ligand, a sodium channel site ligand, and a potassium channel site ligand were synthesized. The binding of these fluorescent ligands was characterized by direct fluorescence measurement.

The equilibrium dissociation constants ($K_D$) estimated by fluorescence monitoring were consistent with values obtained using radioligand binding techniques. The potencies of chemically diverse compounds to inhibit fluorescent ligand binding are highly correlated with potencies obtained from radioligand binding techniques. These findings demonstrate that direct fluorescence measurement techniques can be used to quantitate ligand-receptor interactions. The results indicate that application of fluorescence quenching techniques are a useful adjunct for the study of specific receptors.

DETAILED DESCRIPTION OF THE INVENTION

It has now been discovered that it is possible to bind a fluorescent label to a specific ligand for receptors, especially receptors in the central nervous system (CNS), for use in quantitatively, sensitively and directly detecting binding of the ligand to the receptors, both in vitro in solution or suspension and intracellularly in cells or tissue. The process and reagents are particularly useful in targeting benzodiazepine, cannabinoid, glycine, muscarinic, dopamine, opioid, N-methyl D-aspartate, β- and α-adrenergic, and serotonin receptors, glibenclamide receptors and potassium or sodium channel receptors or sites.

It is important that the fluorescent label be attached to the ligand at an appropriate site so as to not interfere with binding activity of the ligand nor with fluorescence of the label. It is also important to choose a label which emits detectable fluorescence at the desired wavelength(s), under the conditions under which it is to be detected, including pH, ionic strength, polarity of the solution (for example, water versus alcohol versus ethyl acetate), and amount and type of tissue present (for example, brain tissue versus kidney tissue versus lung tissue versus heart).

Advantages to the use of fluorescence include the rapidity with which results can be obtained (less than or equal to milliseconds), allowing use of the label in following binding over time, in contrast to radioactivity, which requires reaching equilibrium (e.g., 60 minutes), then stopping of the reaction (15 to 60 seconds), then a relatively lengthy process (hours to days to months) to make a determination. Other advantages include the ability of some fluorescent labels to fluoresce at different wavelengths with different intensities under different conditions. The latter is useful in determining whether or not the labelled ligand has penetrated into a cell, since the conditions, for example, pH, intracellularly versus extracellularly are quite different. For example, one can also look at lateral mobility, the passage of molecules into and out of cells. This is not possible with radioactive labels. The intensity of some fluorescent labels also declines over time after binding, allowing one to measure binding kinetics with one label. One can also use a quenching ligand to reduce intensity, for example, where more than one fluorescent label has been used, to create a three dimensional structural/activity comparison of a receptor conformation.

The fluorescent labelled ligand can be used directly and quantitatively to measure and locate ligand-receptor interactions. Quantitation is achieved as described in more detail below, by measuring fluorescence at one or more specific wavelengths and comparing intensity with concentration on a standard line. Since the label is bound directly to the ligand which binds directly and specifically to the receptor, and tissue or cells do not have be removed prior to measurement, the assay is direct. This is in contrast to prior uses of fluorescent probes, such as Flura II™ (Molecular Probes, Eugene, OR), which mimics calcium and has been used to measure flux into a cell. In this prior method, measurement requires that there be one or more intermediate steps to determine the presence of and effect on specific receptors.
Fluorescent Labels.

The criteria for selecting an appropriate fluorescent label are that it must not hinder binding by the ligand to the receptor, i.e, the specificity and selectivity of the ligand; and that it must be detectable in the visible spectrum.

Examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. The preferred label is fluorescein (5-carboxyfluorescein-N-hydroxysuccinimide ester) or rhodamine (5,6-tetramethyl rhodamine). NBD is a suitable fluorophore since it is a relatively small apolar molecule that would not be expected to sterically hinder a ligand-receptor interaction if coupled to the parent molecule at an appropriate position using a suitable spacer group. NBD also has a relatively small dipole moment, reducing the possibility of an electrostatic interaction with the pharmacophore which would result in a loss in affinity compared to the parent compound. These can be obtained from a variety of commercial sources, including Molecular Probes, Eugene, Ore. and Research Organics, Cleveland, Ohio.
Ligands.

The label is bound to a ligand known to bind to a receptor with high affinity (the likelihood of a ligand binding to a receptor, measured in terms of concentration), selectivity (rank order of potency of a ligand for a specific receptor as compared with others binding to the same receptor, measured in terms of concentration), and specificity (recognizing only one receptor, as compared to more than one receptor, for example, diazepine recognizes only benzodiazepine receptors and no other receptors, as compared to SCH 23390, which recognizes primarily dopamine type 1 receptors as well as serotonin receptors). Examples of preferred compounds for binding to CNS receptors include benzodiazepine and derivatives and related compounds thereof, procainamide, fluphenazine, anandamide, arachidonic acid, and derivatives thereof, dopamine, opioids, N-methyl D-aspartate (glycine or glutamate), β-adrenergic agonists and antagonists, α-adrenergic agonists and antagonists, and serotonin. As used herein, "ligand" includes bioactive compounds (drugs) or compounds known to bind to a particular receptor which may or may not exert a biological effect as a result of binding. There is no preferred size. The affinity should be less than one micromolar, preferably less than 100 nM.

Procedures for binding label to ligand.

Methods known to those skilled in the art are used to bind the label to the ligand. Examples are provided in detail below. In general, the label is bound to the ligand at a site where the label does not sterically hinder binding of the ligand to the receptor, usually through an amine group, using a protection-deprotection process. The site of attachment of the fluorescent label to the ligand is particularly important as compared with attachment of a radiolabel to the ligand since a radiolabel usually consists of one or two atoms while the fluorescent probe may be of the same size as the ligand and therefore much more likely to interfere with binding to the receptor. The label must also be bound so that the ligand does not significantly interfere with or decrease the fluorescent intensity of the label.

In some cases, to avoid stearic interference, the label is bound to the ligand through a spacer. A preferred spacer is a linear carbon chain. In the preferred embodiment, the spacer consists of a two to seven methylene carbon chain which prevents the label from interfering with the binding activity of the ligand.

Methods for measuring fluorescence.

The excitation and emission spectra of the fluorescent label are measured using commercially available instrumentation, for example, as described below. Quantitation of binding is accomplished by creating a standard line relating fluorescence intensity values (counts/s) to known amounts of fluorescent ligand in a tissue suspension or buffer. The amount of fluorescent ligand bound is estimated by linear regression using fluorescence intensity in tissue suspension versus ligand concentration (nM). The quantity of free ligand is directly assayed from fluorescence intensity measurements in buffer versus ligand concentration.

Displacement of fluorescent ligand binding to membranes or tissue is examined by incubating the ligands in the presence of varying concentrations of several competing compounds and quantitating fluorescence.

Analysis of intracellular events versus extracellular events is accomplished by choosing an appropriate fluorescent probe (e.g., fluorescein) which emits different fluorescent intensities depending on the pH of the environment, labeling the specific ligand with the label, and exposing the cells to the labelled ligand under conditions at which binding can occur. The pH of the inside of the cell is generally known (usually in the range of 7.4). The pH of the extracellular environment can be manipulated as desired to produce a difference in fluorescent intensity. For example, fluorescein has a low fluorescent intensity at pH 6.0 and optimum fluorescent intensity at pH 8.1. The fluorescein is ionized and the different intensities measured to quantitate the amount of intracellular versus extracellular binding.

Quantitation of fluorescent binding can be accomplished by creating a standard line relating fluorescence intensity values (counts/s) to known amounts (between approximately 1 and 1024 nM) of fluorescent ligand in tissue suspension or buffer. The amount of fluorescent ligand bound is estimated by linear regression using fluorescence intensity in tissue suspension versus ligand concentration (nM). The quantity of free ligand is directly assessed from fluorescence intensity measurements in buffer versus ligand concentration.

For determining standardization and quantitation of fluorescent ligand binding, measured as fluorescence intensity (cps) versus labelled ligand concentration in nM, increasing concentrations of fluorescent ligand are added to cuvettes containing cortical tissue suspension (approximately 300 µg protein/assay) or buffer (50 mM Tris-citrate, pH 7.4 at 4° C.).

Ligand Binding.

For association of labelled compound binding to cortical membranes, tissues are incubated at 4° C. for between 1 and 70 minutes in buffer containing labelled compound. Incubations are terminated by centrifugation at 20,000×g for 10 min at 4° C. Under these conditions, equilibrium is attained by 20 minutes. A one hour incubation period is routinely used in other experiments. $LR_e$ is the concentration of ligand bound at equilibrium, and LR is the concentration of ligand bound at each time interval. For dissociation of fluorescent ligand binding, graphs are constructed by plotting ln ($LR/LR_o$) versus time, where $LR_o$ represents the concentration of ligand-receptor complex before initiating dissociation.

Fluorescence Assays

Tissue suspensions (2 ml) are incubated in 1-cm acrylic cuvettes (22°–23° C.) with constant stirring. Stock solutions of labelled compounds and drugs are diluted in buffer and added (in 10 µl aliquots) sequentially as indicated to yield the desired final concentrations. The final concentration of $Me_2SO$ in the assay is less than or equal to 0.006%. This concentration of $Me_2SO$ has no detectable effect on ligand binding to benzodiazepine receptors. The sample is excited at 486 nm, and emission is monitored at 542 nm with narrow band-pass slits and cross polarizers to minimize light scattering.

Protein Determination

Protein content is determined using the method of Miller, G. *Anal. Chem.* 31, 964–971 (1959) with bovine serum albumin as a standard.

The fluorescent behavior of labelled compound in the presence of receptors is examined by exciting tissue and ligand with monochromatic light (486 nm) and monitoring emission intensity (542 nm) at 1–s intervals. After determining background tissue fluorescence (autofluorescence), compound is added to the stirred membrane suspension. Fluorescence is measured for labelled compound alone (C) and in the presence of other drugs (D). The difference in fluorescence intensity between D and C (D–C) represents the amount of fluorescence that can be specifically dequenched by an excess of receptor ligands but not other compounds and is referred to as "specific quenching."

The fluorescent labelled ligand can be used to screen compounds for specific binding to a receptor, either intracellularly or extracellularly, as described above, by competitive binding of the labelled ligand with the compound to be tested. Known concentrations of both labelled ligand and compound to be screened are added to the cells containing the receptor (or a solution, suspension or immobilized substrate containing receptor) under conditions at which binding should occur. The displacement of the labelled ligand is used to determine and quantitate the binding of the compound to be screened to the receptor.

The following examples demonstrate the use of a newly synthesized fluorescent ligand to study kappa$_1$ opioid receptors, N-methyl-D-aspartate receptors, and potassium channel receptors in a disrupted membrane preparation.

The present invention will be further understood by the following non-limiting examples. The abbreviations used herein are: KOH, potassium hydroxide; TEA, triethanolamine; DCC, N,N'-dicyclohexylcarbodiimide; H-NMR, proton nuclear magnetic resonance; IR, infra-red spectroscopy; DMF, N,N-dimethylformamide; BZ, benzodiazepine; CNS, central nervous systems; EIMS, electron ionization mass spectra; HRMS, high-resolution mass measurements; TLC, thin-layer chromatography; CIMS, chemical ionization mass spectra; NBD, 7-nitrobenz-2-oxa-1,3-diazole; FW, formula weight; THF, tetrahydrofuran. The teachings of the references cited in the following examples are specifically incorporated herein.

TABLE I

| Photofluor | Product # | Parent Compound | Dye Name | Fluores. Kd (nM) | Radiolig. Kd:Ki (nM) | Bmax (pmol/mg prot.) | Separation Methods |
|---|---|---|---|---|---|---|---|
| Cannabinoid | PDC 014.063 | anandamide | NBD deriv. | | 52 | | centri., quench |
| Cannabinoid | PDC 014.064 | anandamide | dansyl deriv. | | 52 | 69 | centri., spectral shift |
| Dopamine 1 | PDC 014.043 | fluphenazine analog | NBD deriv. | 190 | 11 | | centri., quench |
| Dopamine 2 | PDC 014.036 | metoclopramide | NBD deriv. | 500 | 90 | 0.13 | centri., quench |
| Glycine | PDC 002.083 | 5,7DCKA | NBD deriv. | 750 | 69 | 14.5 | centri., quench |
| Muscarinic-M1 | PDC 018.039 | minaprine | NBD deriv. | 985 | 1700 | 0.20 | centri., quench |
| Muscarinic-M2 | PDC 014.034 | AQ-RA 741 analog | NBD deriv. | 1010 | 10 | 10 | centri., quench |
| NMDA | PDC 014.041 | MK 801 analog | dansyl deriv. | 1000 | 45 | 1.9 | centri., spectral shift |
| Kappa 1 | PDC 018.083 | U50,488 analog | fluorescein deriv. | 10 | 200 | 0.04 | centrifugation |
| Peripheral Bzd | PDC 018.091 | PK 14105 analog | fluorescein deriv. | 40 | 2 | 2.3 | centrifugation |
| Potassium Channel | PDC 018.066 | glibenclamide | NBD deriv. | 1030 | 1 | 0.40 | centri., quench |
| Sodium Channel | PDC 014.071 | procainamide | dansyl deriv. | | | | centri., spectral shift |
| Adenosine-A2a | PDC 018.075 | CGS 21680 | fluorescein deriv. | 57 | 15 | 2.3 | centrifugation |

Notes to Table I.
Separation Methods:
(1) Centrifugation
(2) Quench—Fluorescence can be quenched by binding of the ligand in the cavity of the receptor, and resurges when the ligand is expelled from the cavity, e.g., by a competitive inhibitor. This can be measured in situ.
(3) Spectral shift—The fluorescence may shift on binding of the ligand, usually to a longer wavelength. This can be measured in situ.

Bmax: Density of binding of the ligand measured in pmol/mg protein.

EXAMPLE 1

Synthesis of kappa$_1$ opioid fluorescent probes.

(a) 1S,2S-trans-4,5-dichloro-2-(4-fluorescein-5-carboxamido)-n-butananido)-(N-methyl)-2-(1-pyrrolidinyl)-cyclohexyl)benzeneacetamide To carboxyfluorescein-succinimide ester, 37.6 mg (0.079 mmol) in dry DMF (1.0 ml) was added 1S,2S-trans-2-(4-(amino)-n-butananido)-4,5-dichloro-(N-methyl)-2-(1-pyrrolidinyl)cyclohexyl)benzeneacetamide (51.7 mg, 0.095 mmol, FW=542.4 g/m) followed by TEA, 106 μl (8.0 eq) and the solution was stirred overnight at room temperature and the solvent stripped off under high vacuum. The oily residue was separated by preparative TLC on two 20 cm×20 cm×1 mm plates developed with 5:45:50 NH$_4$OH/MeOH/CHCl$_3$. Yield=49 mg of orange powder, FW=842 g/m.

This compound was tested for binding to receptor in tissue by measurement of fluorescence. The inhibitory constant (ICO) versus radioligand binding ([$^3$H]U69,593, ref: Lahti et al., "[$^3$H]U-69593 A Highly Selective Ligand for the opioid kappa Receptor", *European Journal of Pharmacology*, 109, 281,284 (1985) was 0.85 nM. The affinity constant (K) of PDC 909 as determined by direct fluorescence measurement was 10 nM.

1R,2R-trans-4,5-dichloro-2-(4-fluorescein-5-carboxamido)-n-butaniado)-(N-methyl)-2-(1-pyrrolidnyl)-cyclohexyl)benzeneacetamide To a solution of carboxyfluorescein-succinimide ester (50 mg) in dry DMF (1 ml) was added 1R,2R-trans-2-(4-(amino)-n-butananido)-4,5-dichloro-(N-methyl)-2-(1-pyrrolidinyl)cyclohexyl)benzeacetamide (68.7 mg, 1.2 eq, FW=542.4 g/m), followed by TEA 141.3 mg (8.0 eq) and the solution stirred overnight at room temperature. The residue found after evaporation of the DMF was applied to two 20 cm×20 cm×1 mm TLC plates and the plates developed with 5:45:50 NH$_4$OH/MeOH/CHCl$_3$ to give an orange powder. Yield=52 mg, FW=842 g/m.

This compound is the less active enantiomer. IC$_{50}$ value versus radioligand binding ([$^3$H]U69,593) was 3229 nM (greater than 1 μM). Measurement using the fluorescence assay confirmed the radioligand results.

(b) Synthesis of PDC018.083

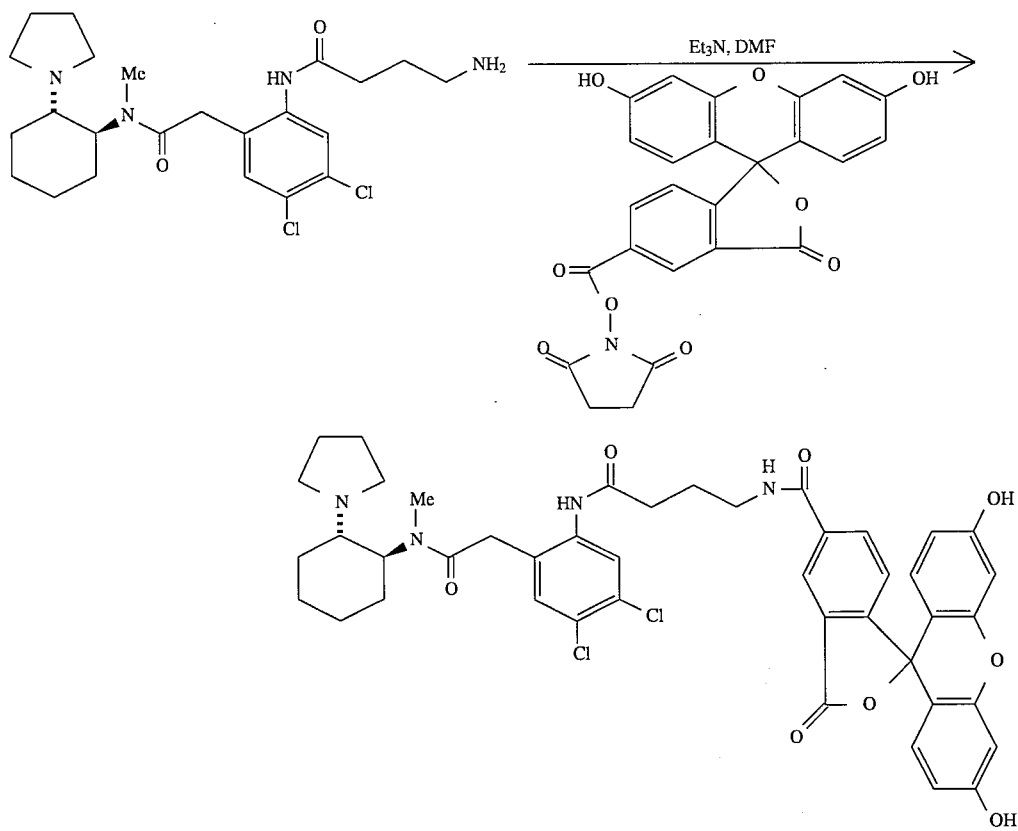

To carboxyfluorescein-succinimide ester (37.6 mg, 0.079 mmol) in DMF (1.0 mL) was added 1S,2S-trans-2-(4-amino-n-butananido)-4,5-dichloro-(N-methyl)-2-(pyrrolidinyl-cyclohexyl)benzeneacetamide (51.7 mg, 0.095 mmol) followed by TEA (106 μL, 8 equivalents) and the solution was stirred overnight at room temperature. The solvent was removed in vacuo to yield an oily residue. The product was isolated by preparatory TLC (5:45:50 NH$_4$OH/MeOH/chloroform) to yield PDC018.083 (49 mg) as an orange powder.

EXAMPLE 2

Synthesis of potassium channel fluorescent probes.

(a) 4-[[[(cyclohexylamino)carbonyl]amino]sulfonyl]phenyl ethylamine, XIV

One equivalent of 4-(2-aminoethyl)benzensulfonate (Aldrich) was dissolved in acetone containing 1.2 equivalents potassium carbonate (Aldrich). This solution was heated to reflux upon which 1.2 equivalents cyclohexyl isocyanate (Aldrich) dissolved in acetone was added dropwise. After 12 hours, white precipitate formed which was filtered, washed with acetonitrile and recrystallized from ethanol and water. Thin layer chromatography indicated purity and proton NMR was consistent with the structure proposed.

4-[4-[[[(cyclohexylamino)carbonyl]amino]sulfenyl]phenyl ethylamino]-7-nitrobenzofurazan, XV One equivalent XIV was dissolved in 10% aqueous sodium bicarbonate with stirring under air 1.2 equivalents NBD-chloride was added and after 12 hours the yellow crystals were dissolved giving a dark orange solution. The aqueous layer was extracted with diethyl ether, the ether evaporated and the product was recrystallized from ethanol and water.

(b) Glibenclamide analogue coupled to p-(S-dimethylaminonaphthalene-1-sulfonyl-aminophenyl) -isothiocyanate (PDC014.008)

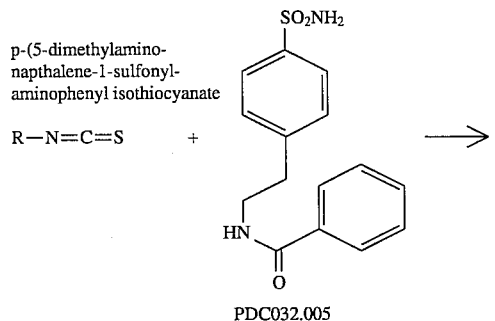

p-(5-dimethylamino-napthalene-1-sulfonyl-aminophenyl isothiocyanate

R—N=C=S +

PDC032.005

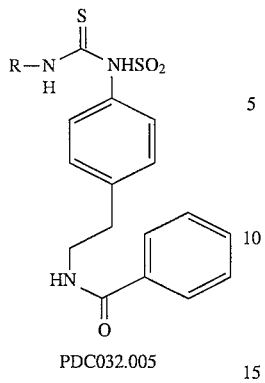

PDC032.005

Preparation of PDC032.001 (Batch no. .005)

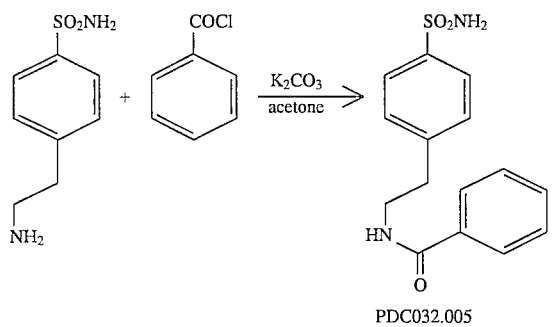

PDC032.005

The sulfonamide (20 grams, 0.1 mol) was dissolved in acetone (700 mL) and potassium carbonate (16.6 grams, 0.12 mol) was added. A solution of benzoyl chloride (16.9 grams, 0.12 mol) in acetone (200 mL) was added over a period of 45 minutes. A white solid precipitated during the addition. The reaction mixture was stirred at room temperature for 24 hours. The reaction mixture was worked up by adding water, and extracting the product into ethyl acetate. The solvent was removed in vacuo to yield a brown residue. The residue was crystallized from ethanol/water to yield PDC032.005 (14.28 grams) as white needles.

Preparation of PDC014.008 p-(5-dimethylamino-
napthalene-1-sulfonyl-
aminophenyl isothiocyanate

R—N=C=S    +

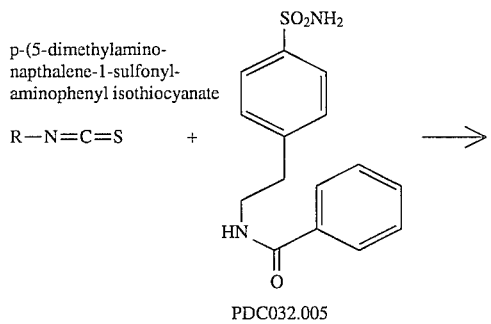

PDC032.005

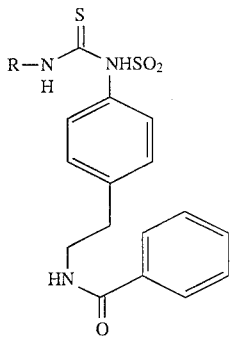

The sulfonamide (PDC032.001) (0.03 grams, 0.099 mmol) and NaH (0.003 grams, 0.128 mmol) were dissolved in DMF (2 mL) as a solution of DANSAPI [p-(5-dimethylamino-naphthalene-1-sulfonyl-amino phenyl isothiocyanate] (0.049 gram, 0.128 mmol) in DMF was added. The reaction mixture was heated to 50° C and stirred for 16 hours. The DMF was removed in vacuo, and the fluorescent residue was purified by preparatory TLC (1:9:40 NH$_4$OH/MeOH/CHCl$_3$). The resulting product was re-purified by preparative TLC (1:9:40 NH$_4$OH/MeOH/CHCl$_3$) to yield PDC014.008 (4.1 mg) as a fluorescent yellow solid.

EXAMPLE 3

Synthesis of glibenclamide fluorescent probes.

4-(5-hydroxylamino)-7-nitrobenzofurazan, XVI

To one equivalent NBD-Chloride (Aldrich) in THF at RT under nitrogen was added dropwise simultaneously from two separate addition funnels 1.1 equivalents 5-amino-1-pentanol (Aldrich) and 1.0 equivalents triethylamine (Aldrich). After 24 hours filter solids, rotovap solvent and purify by column chromatography (silica, 25% ethylacetate in hexanes). Proton NMR was consistent with structure proposed and material was pure by thin layer chromatography (RF 0.3, silica, 25% ethylacetate/hexanes).

4-(5-(p-toluene sulfonato)amino)-7-nitrobenzofurazan, XVII

One equivalent XVI was dissolved in acetonitrile to which 1.25 equivalents sodium carbonate was added. The suspension was heated to reflux and 1.1 equivalents p-toluenesulfonyl chloride in acetonitrile was added dropwise from an additional funnel. The reaction mixture was filtered to remove the sodium carbonate and the solvent was evaporated.

The residue was dissolved in diethylether and extracted with water to remove unreacted starting material. The proton NMR spectrum was consistent with the proposed structure.

2-Nitrobenzoyl-[4-[[[[cyclohexylamino)carbonyl] amino]sulfonyl]phenylethylamine, XVIII One equivalent of the sulfonate (XIV) was dissolved in acetone, 1.1 equivalents sodium carbonate was added and the suspension heated to reflux. 1.1 equivalents 2-nitrobenzoylchloride (Aldrich) was dissolved in acetone and added dropwise to the refluxing mixture. After 5 hours the reaction was allowed to cool to room temperature, the sodium carbonate removed by filtration and the acetone evaporated. The residue was dissolved in diethylether and washed with water. After evaporating the diethylether, the product was recrystallized from ethanol and water. Proton NMR was consistent with the proposed structure.

2-Aminobenzoyl-[4[[[(cyclohexylamino)carbonyl]amino]sulfonyl]phenyl ethylamine, XVIIII Compound XVIIII was produced in quantitative yield by hydrogenating over platinum dioxide in methanol. Platinum dioxide was filtered and methanol was evaporated. Recrystallization from ethanol/water resulted in crystals whose proton NMR was consistent with the proposed structure.

2-(4-(7-Nitrobenzofurazanyl)aminohexyl)aminobenzoyl-[4[[[(cyclohexylamino)carbonyl]amino]sulfonyl]phenylethylamine, XX One equivalent of the aromatic amine was dissolved in acetonitrile to which was added anhydrous potassium carbonate (Aldrich). The reaction mixture was brought to reflux and 1.2 equivalents of the toluenesulfonate (XVII) in acetonitrile was added dropwise. After 5 hours the potassium carbonate was filtered off, the acetonitrile evaporated and the orange residue recrystallized from ethylacetate/hexanes. Proton NMR was consistent with the structure proposed and the material was pure by TLC.

3-(4-(7-Nitrobenzofurazanyl)aminohexyl)aminobenzoyl-[4[[[(cyclohexylamino)carbonyl]amino]sulfonyl]phenylethylamine, XXI Compounds XXI and XXII were prepared in a similar manner using 3-nitrobenzoylchloride and 4-nitrobenzoylchloride, respectively, instead of 2-nitrobenzoylchloride. Spectra were consistent with the structures proposed. 4-(4-(7-Nitrobenzofurazanyl)aminohexyl)aminobenzoyl-[4[[[(cyclohexylamino)carbonyl]amino]sulfonyl]phenylethylamine, XXII Compounds were assayed using radioligand binding methods ([$^3$H]glibenclamide, ref: Zini et al., "Two binding sites for [$^3$]glibenclamide in the rat brain", *Brain Research*, 542, 151–154 (1991) ($IC_{50}$ less than 1000 nM). The fluorescently labeled compounds were also assayed in the fluorescence assay.

EXAMPLE 4

Synthesis of N-methyl-D-aspartate Strychnine-insensitive glycine receptor fluorescent probes.

4-(6-tert-Butoxycarbonyl)-diamino-1-hexyl)-7-nitrobenzofurazan, III

To two equivalents mono-N-(tert-Butoxycarbonyl)-1,6-diaminohexane - hydrochloride (I) (Fluka) dissolved in 10% aqueous sodium bicarbonate solution was added one equivalent NBD-chloride (II), 4-chloro-7-nitrobenzofurazan, Aldrich).

NBD-chloride crystals did not dissolve immediately, but after 24 hours at room temperature under air the reaction mixture turned dark orange and brown solids formed on the walls of the flask. The reaction mixture was diluted with equal parts diethyl ether and distilled water. The ether layer was separated and washed with water several times to remove the hydrochloride salt, then dried over sodium sulfate. The ether was removed under vacuum, resulting in a brown-black film which could be scraped easily from the walls of the flask. This material was pure by thin layer chromatography Rf=0.75 (silica, 1:9:90 ammonium hydroxide, methanol, chloroform) and had a melting point of 58°–61° C.

4-(1,6-diaminohexyl)-7-nitrobenzofurazan trifluoroacetate, V

The NBD—substituted hexane diamine (III) was deprotected by stirring for 12 hours at room temperature in excess trifluoracetic acid (IV, Aldrich). The excess trifluoroacetic acid was removed under a stream of nitrogen, resulting in a brown residue which was washed with diethyl ether to remove unreacted III. This material was carried on to the next step without further purification.

5,7-Dichlorokynurenic acid-4-nitrophenyl ester., VIII 5,7 - Dichlorokynurenic acid (VI) (Research Biochemicals) was activated for further reaction with the amine (v) as follows: one equivalent of VI was treated with 2.7 equivalents of 4-nitrophenyltrifluoroacetate (VII, Aldrich) in dimethylsulfoxide with a catalytic amount of pyridine. The reaction mixture was stirred at room temperature under air for 12 hours after which water was added to crystallize the 5,7-dichlorokynurenic acid nitrophenylester (VIII). The crystals were washed with water to remove DMSO, pyridine and trifluoroacetic acid. This material was carried to the next step without further purification.

1-(5,7-dichloro-4-hydroxy-2-quinoline carboxamido)-4-(6-aminohexyl)-7-nitrobenzofurazan, IX, CAR I.083

One equivalent of activated ester (VIII) and 1.4 equivalents of the trifluoroacetate salt (V) were dissolved in DMSO with stirring. Two equivalents 4-methyl morpholine (Fluka) were added in one shot to produce the free amine. The reaction was stirred at room temperature under air for 12 hours after which cold water was added to crystallize the product. An orange solid was formed which was washed with water to remove the 4-nitrophenol byproduct. TLC (silica, 1:9:90 ammonium hydroxide, methanol, chloroform) showed a new fluorescent product at Rf=0.2 with no phenol (Rf=0.5) or other material present.

1-(5,7-dichloro-4-hydroxy-2-quinoline carboxamido 6-aminohexyl-4-(prolyl)-7

Another glycine probe was prepared which consisted of 5,7-dichlorokynurenic acid connected to the same diaminohexane with proline inserted between the NBD fluorophore and diaminohexane. This material was prepared in a similar manner to IX and was pure by thin layer chromatography.

The $IC_{50}$ versus radioligand ([$^3$H]5,7DCKA) binding was greater than 1 µM. On the basis of the criteria specified above, this compound was inactive for the strychnine-insensitive glycine receptor associated with the N-methyl-D-aspartate complex.

4-(6-chloroacetyl-diamino-1-hexyl)-7-nitrobenzofurazan, XI

One equivalent of compound (V) was mixed with 1.2 equivalents chloroacetyl chloride (Aldrich) in acetonitrile with 2 equivalents 4-methylmorpholine (Fluka). The reaction mixture was refluxed overnight. Water was added to precipitate the product and the crystals were washed with water to remove the excess chloroacetylchloride and base.

5,7-Dichloro-4-oxo-(2-acetamido-4-(6-aminohexyl)-7nitrobenzofurazan)-2quinoline carboxylic acid, XII One equivalent 5,7-Dichlorokynurenic acid was dissolved in 10% aqueous sodium bicarbonate with stirring. 2.0 equivalents of acetyl chloride (XI) was added to the flask in one volume. It did not dissolve immediately, but after 12 hours, the reaction mixture was dark orange with no solids present. The reaction mixture was neutralized with 2M hydrochloric acid with cooling and extracted with diethyl ether. The ether was removed under vacuum and the orange solid was recrystallized from ethanol and water. The proton NMR was consistent with the proposed structure.

4-(6-(2-aminoethyl)-diamino-1-hexyl)-7-nitrobenzofurazan, XII

One equivalent of the trifluoroacetate salt (V) was dissolved in acetonitrile with 3 equivalents 4-methyl morpholine (Fluka) in acetonitrile. The reaction mixture was heated to reflux at which time one equivalent 2-bromoethylamine hydrobromide dissolved in acetonitrile was dropped in from an addition funnel. The reaction mixture was stirred at reflux for 8 hours. After cooling, the acetonitrile was removed on a rotary evaporator. The residue was taken up in diethyl ether and extracted with 10% aqueous sodium bicarbonate to remove 4-methylmorpholine. This material was isolated as the free base and was pure by thin layer chromatography (Rf=0.55, silica, 1:9:90 ammonium hydroxide, methanol, chloroform).

1-(5,7-Dichloro-4-hydroxy-2-quinoline carboxamidoethyl amino)-4(6-aminohexyl)-7-nitrobenzofurazan, XIII The final compound XIII was produced by coupling the amine to VIII in a manner identical to the last step in IX. This material is an orange solid and is pure by thin layer chromatography. Although IX was active and useful in an assay for binding as measured using the fluorescent label, XIII was not useful. The binding as measured by fluorescence is approximately nM; the binding as measured with a radiolabel is approximately 60 to 100 nM. These are comparable values. $IC_{50}$ for radioligand binding of ($[^3H]$5,7-dichlorokynurenic acid, ($[^3H]$5,7 DCKA) is reported by Baron et al., "$[^3H]$5,7-Dichlorokynurenic acid, a novel radioligand labels NMDA receptor associated glycine binding sites, *European Journal of Pharmacology*, 206 (1991) 149–154.

EXAMPLE 5

Synthesis of cannabinoid receptor fluorescent probes (a) Anandamide derivative coupled to an NBD derivative (PDC014.063 a)

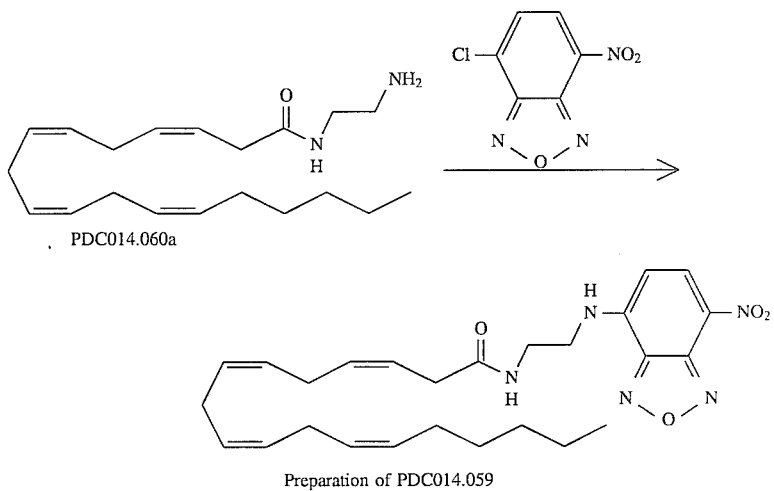

PDC014.060a

Preparation of PDC014.059

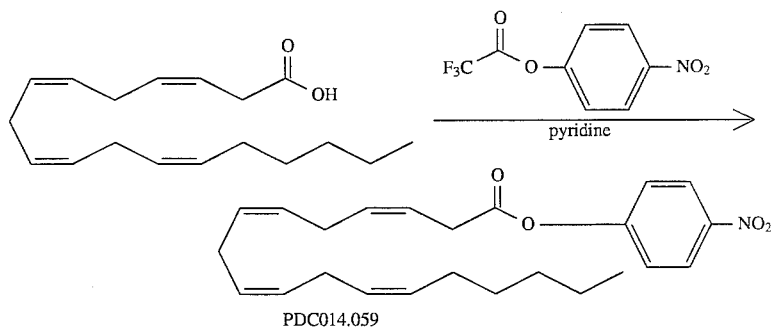

PDC014.059

Arachidonic acid (1 gram, 3.28 mmol) was dissolved in pyridine (16 mL). p-Nitrophenyltrifluoroacetate (0.772 grams, 3.28 mmol) was then added to the solution. The reaction mixture was stirred at room temperature overnight and then the reaction was quenched by adding water (50 mL). The product was extracted into ether (3×100 mL), and the combined ether extracts were washed with water (3×50 mL). Residual p-nitrophenol was removed by washing the ether extracts with saturated aqueous potassium carbonate and water. Residual pyridine was removed by washing the ether extracts with an aqueous citric acid solution and water. The ether was dried and removed in vacuo to yield a pale brown oil (1.315 g, 94%).

Preparation of PDC014,060 a

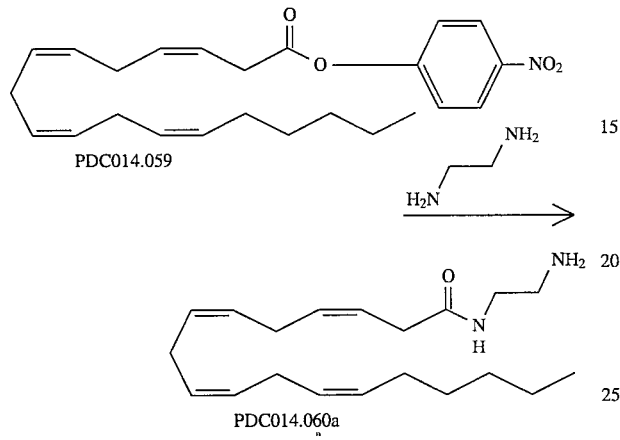

A solution of nitrophenol ester (PDC014.059) (0.66 grams, 1.55 mmol) in chloroform (10 mL) was added dropwise to a solution of ethylenediamine (0.932 grams, 15.5 mmol, 10 equivalents) in chloroform (15 mL). A yellow precipitate of nitrophenol formed during the addition. After three hours, TLC (1:9:90 $NH_4OH/MeOH/CHCl_3$) indicated complete reaction. The solvent was removed in vacuo, and the residue was dissolved in diethyl ether. The ether solution was washed with saturated sodium carbonate solution, then extracted with a citric acid solution. The aqueous phase was basified with a saturated ammonia solution, and extracted with ether. The ether layer was then washed with water and evaporated to yield a pale yellow oil (0.3829 grams, 71%), which appeared to be greater than 99% pure by TLC.

Preparation of PDC014.063 a

Triethylamine (0.195 grams, 0.58 mmol, 1.5 equivalents) was added to a stirred solution of PDC014060 (0.200 grams, 0.58 mmol) and NBD-Cl (0.077 g, 0.385 mmol) in chloroform (3 mL). The solvent was removed under vacuum, the triethylamine azeotropically distilled with ethanol, and the remaining solvent was removed under high vacuum. The resulting solid was dissolved in chloroform and purified by preparatory thin layer chromatography (preparatory TLC) (1:9:90 $NH_4OH/MeOH/CHCl_3$). The product was extracted from the silica gel fractions with methanol, and concentrated in vacuo to give a yellow brown solid. This solid was re-chromatographed to give an orange solid, which was re-crystallized from a mixture of chloroform/hexane to yield an orange crystalline solid (0.0435 grams, m.p. 94.5°–95.0° C.).

(b) Anandamide derivative coupled to a Dansyl derivative (PDC014.064)

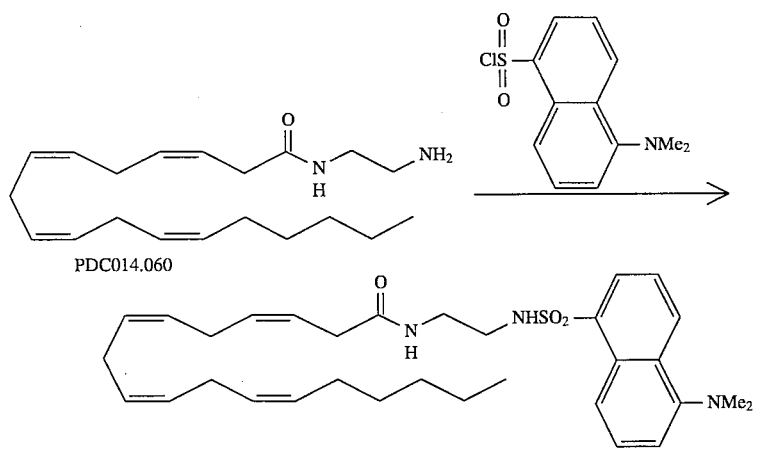

A solution of dansyl chloride (0.13 grams, 0.48 mmol) and PDC014.060 (0.184 grams, 0.53 mmol, 1.2 equivalents) in chloroform (5 mL) and triethylamine (two drops) was stirred at room temperature for 1 hour. The solvent was removed under high vacuum to give an oil. Preparative TLC (1:9:40 $NH_4OH/MeOH/CHCl_3$) gave PDC014.064 (0.1418 grams, 51% based on dansyl chloride) as a pale yellow oil. The proposed structure of this compound was confirmed by NMR.

EXAMPLE 6

Synthesis of dopamine$_1$ and dopamine$_2$ receptor fluorescent probes

(a) Dopamine₁—Fluphenazine analog coupled to an NBD derivative (PDC014.043)

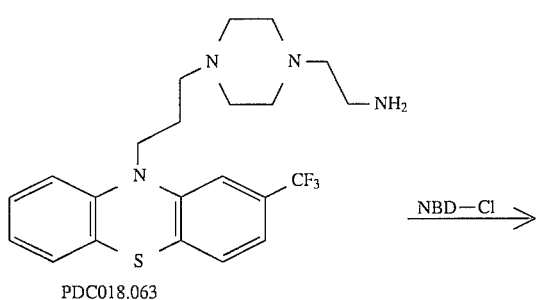

Preparation of PDC018.061

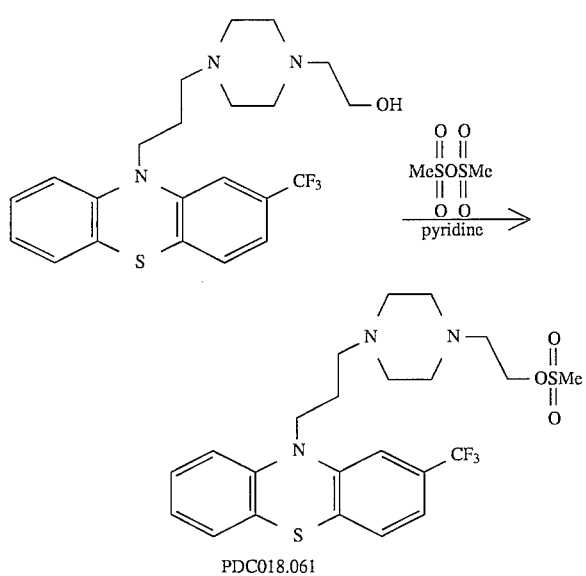

A solution of free base (0.86 grams, 1.96 mmol) in pyridine (5 mL) was added to a solution of methane sulfonic anhydride 1.02 grams, 5.9 mmol, 3 equivalents) in pyridine (5 mL) and the reaction was stirred at room temperature for 30 minutes. TLC showed an incomplete conversion, so additional methane sulfonic anhydride was added. The reaction was quenched by adding saturated aqueous sodium bicarbonate (100 mL). The product was extracted into ethanol (2×150 mL), and the combined organics were washed with 10% aqueous sodium bicarbonate solution. The organics were dried over sodium sulfate, and the solvent was removed in vacuo to yield 0.800 grams of a brown oil which was used without purification in subsequent chemistry.

Preparation of PDC018.063

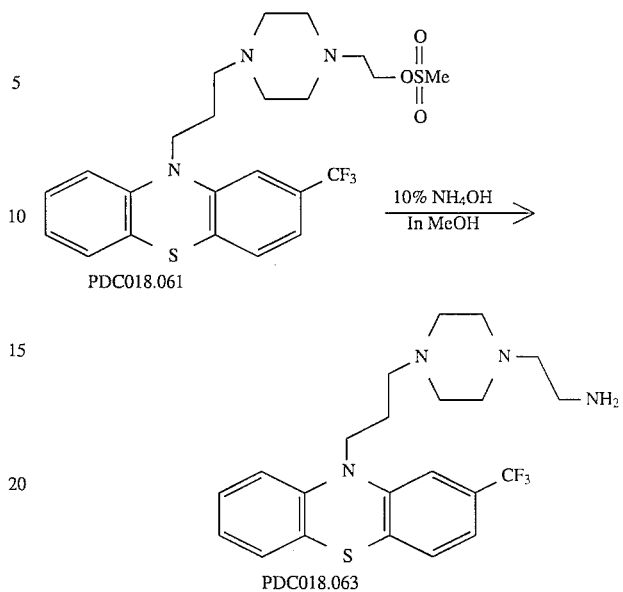

The mesylate (0.6 grams) was placed in 10% ammonia in methanol (10 mL) and allowed to stir at room temperature over a weekend. The compound was purified by preparative TLC (1:9:40 NH₄OH/MeOH/CHCl₃) to give PDC018.063 as a mostly pure (around 90%) material which was used without further purification in subsequent chemistry.

Preparation of PDC014.043

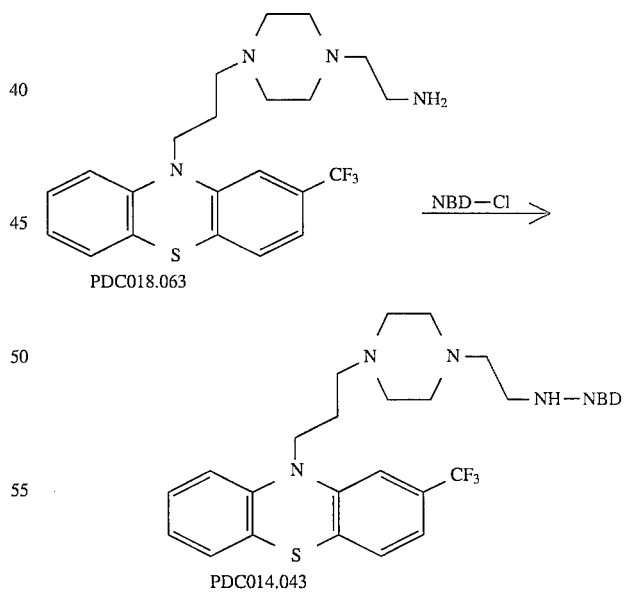

A solution of I (PDC018.063) (0.045 mg, 0.103 mmol) and NBD-Cl0.013 mg, 0.065 mmol) in DMF was stirred at room temperature overnight. The DMF was removed under high vacuum and the resulting solid black residue was purified by preparatory TLC (1:9:90 NH₄OH/MeOH/CHCl₃) to yield II as an orange solid.

(b) Dopamine₂—Metoclopramide derivative coupled to an NBD derivative (PDC014.036)

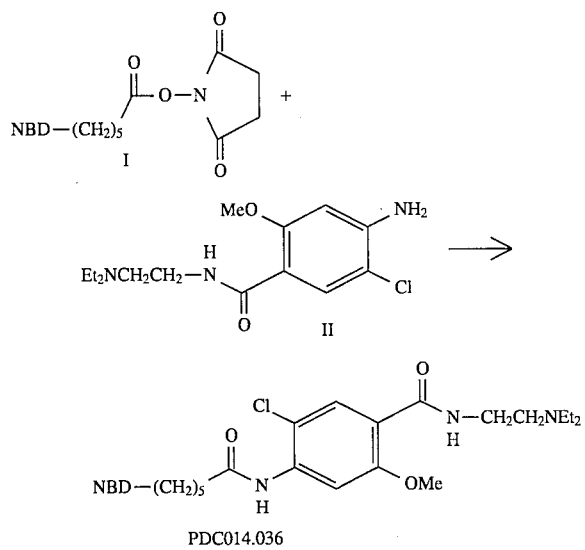

PDC014.036

A solution of I (10 mg, 0.026 mmol) and II (20.0 mg, 0.051 mmol) in DMF (2 mL) was stirred overnight at room temperature, then heated to between 75 and 80° C until the starting material was consumed, as shown by TLC (1:9:40 NH₄OH/MeOH/CHCl₃). The DMF was removed in vacuo and the resulting solid residue was purified by preparative TLC (1:9:40 NH₄OH/MeOH/CHCl₃), yielding two compounds. Both compounds were removed from the silica with 10% ammonia/methanol. The solvent was removed and both fractions analyzed by NMR. PDC014.036 was the product with the lower Rf, as confirmed by NMR.

EXAMPLE 7

Synthesis of a glycine receptor fluorescent probe (PDC002.083)

a) Preparation of NBDNH(CH2)6NH₂·TFA

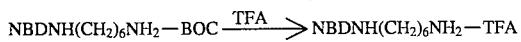

NBDNH(CH2)6NHBOC (0.1191 grams, 0.31 mmol) was dissolved in trifluoroacetic acid (2 mL, large excess) and stirred at room temperature overnight. TLC (1:9:90 NH₄OH:MeOH:chloroform) indicated complete reaction. The trifluoroacetic acid was removed by applying a stream of nitrogen gas to the solution to yield the TFA salt. The crude material was dissolved in acetone and precipitated with diethyl ether to form NBDNH(CH2)6NH₂·TFA as a brown needle-like crystalline solid (m.p. 101°–107° C.).

b) Preparation of the p-nitrophenyl ester of dichlorokynurenic acid

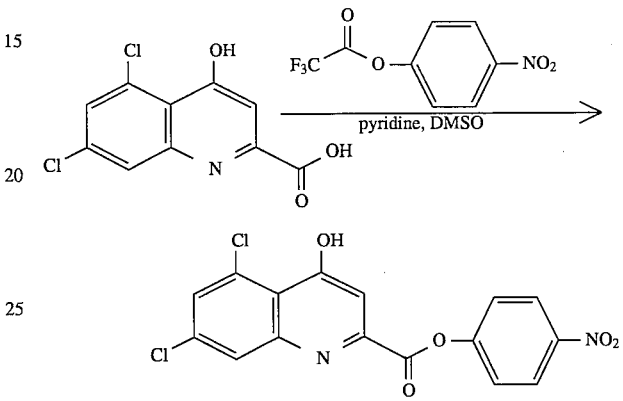

A solution of dichlorokynurenic acid (0.0232 grams, 0.012 mmol) and p-Nitrophenyltrifluoroacetate (0.0585 grams, 0.025 mmol (2.9 equivalents) in DMSO (0.4 mL) and pyridine (0.1 mL) was stirred for 8 hours. The reaction was quenched with water. The solvent was removed in vacuo to give the nitrophenyl ester (0.0285 grams, 83%).

c) combining NBDNH (CH2) 6NH₂. TFA with the nitrophenyl ester.

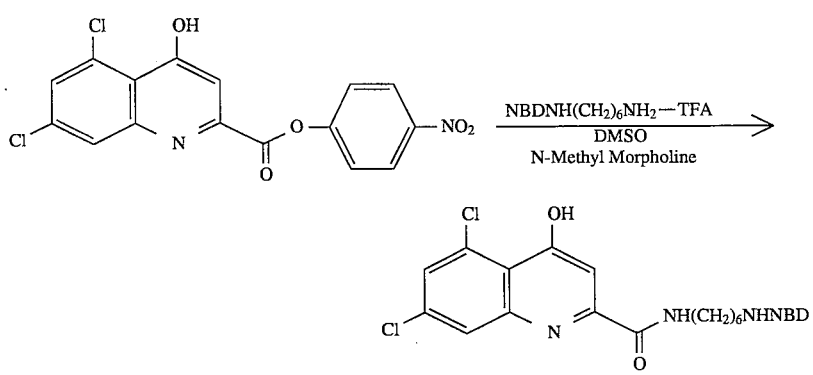

N-methyl morpholine (15 μL) was added to a solution of the TFA salt (0.0359 grams, 0.091 mmol) and the p-nitrophenyl ester (0.0261 grams, 0.066 mmol) in DMSO (0.5 mL). The reaction mixture was stirred at room temperature overnight under air.

The solution was filtered through glass wool into tubes containing cold water (0.75 mL). The solvent was removed by vortex spinning to yield orange crystals. The crystals were washed three times with cold water to remove the p-nitrophenol by-product, giving PDC002.083 as an orange solid.

EXAMPLE 8

Synthesis of muscarinic$_1$ and muscarinic$_2$ receptor fluorescent probes.

(a) Muscarinic$_1$—Minaprine derivative coupled to an NBD derivative (PDC018.039)

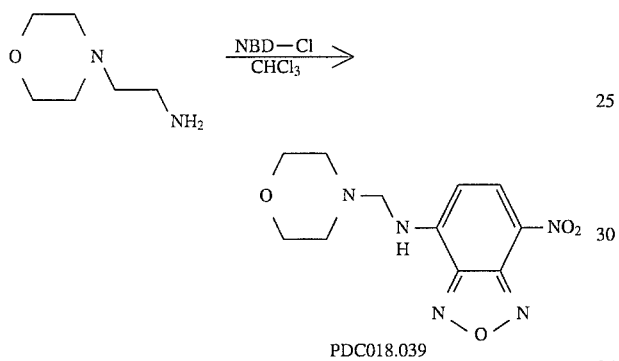

PDC018.039

4-aminoethylmorpholine (1 gram, 0.00768 mmol) and NBD-Cl (0.77 grams, 0.00384 mmol, 0.5 equivalents) were dissolved in chloroform (25 mL) and stirred at room temperature for 48 hours. Residual aminoethylmorpholine was removed by extracting the chloroform with water. The organic solution was then filtered through a 1.5 inch plug of silica gel (1:9:90 NH$_4$OH/MeOH/CHCl$_3$) and extracted with 10% aqueous ammonia and water. The chloroform was removed in vacuo to give 0.8 grams of a brown oil. The oil was purified by preparative TLC (1:9:90 NH$_4$OH/MeOH/CHCl$_3$), and the product was extracted from the silica gel with a solution of 10% ammonia in methanol. The methanol was removed in vacuo to yield PDC018.039 (0.1089 grams) as an orange powder.

(b) Muscarinic$_2$—AQ-RA 741 analog coupled to an NBD derivative (PDC014.034)

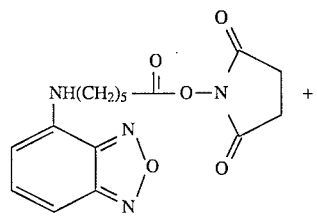

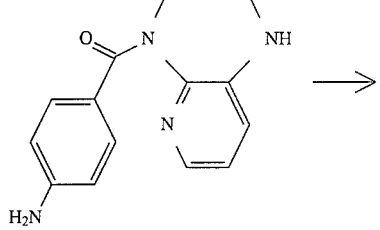

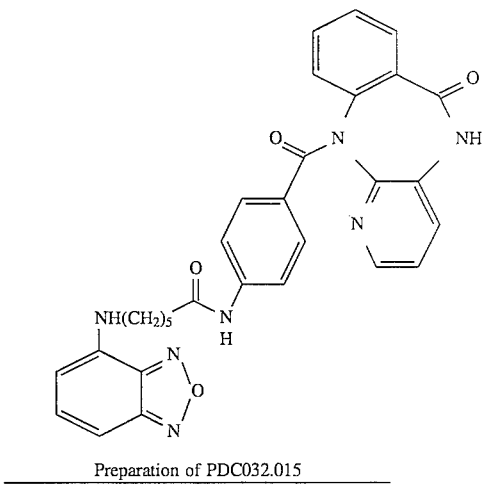

Preparation of PDC032.015

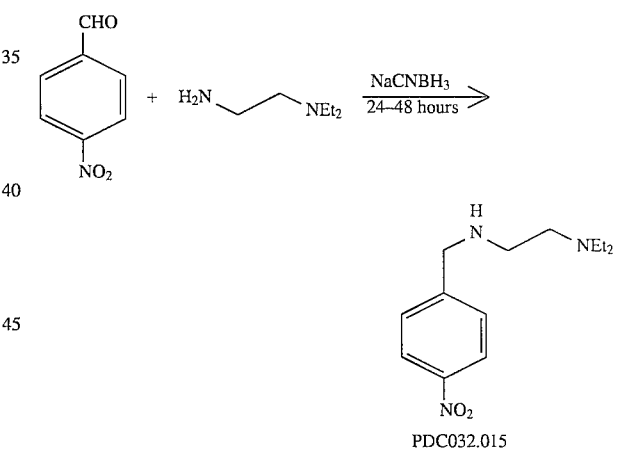

PDC032.015 p-nitrobenzaldehyde (6.5 grams, 43 mmol) and N,N-diethylethylene-diamine (25 grams, 215 mmol) were dissolved in ethanol and the volume of the solution was made up to 250 mL by adding additional ethanol. Glacial acetic acid (20 mL) was added to this solution, and an argon atmosphere was established. NaCNBH$_3$ (10.7 grams, 169.7 mmol) was added in one portion, and rapid effervescence was observed. The mixture was stirred at room temperature overnight. When TLC (1:9:90 NH$_4$OH/MeOH/CHCl$_3$) indicated complete consumption of the aldehyde, the reaction mixture was concentrated in vacuo to give a brown residue. The residue was dissolved in water and acidified with acetic acid. The solution was then extracted with diethyl ether (2×200 mL) to remove neutral impurities. The aqueous layer was basified with 15% aqueous sodium hydroxide, and extracted with ether. The ether fractions were evaporated down to an oil, and residual water was removed by azeotropic distillation with absolute ethanol to yield PDC032.015 as an oil (9.55 grams) which showed one spot by TLC (1:9:90 NH₄OH/MeOH/CHCl₃).

Preparation of PDC032.080

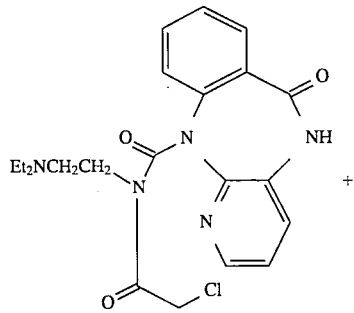

+

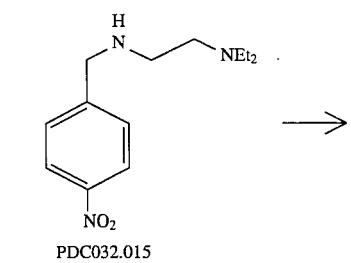

PDC032.015

→

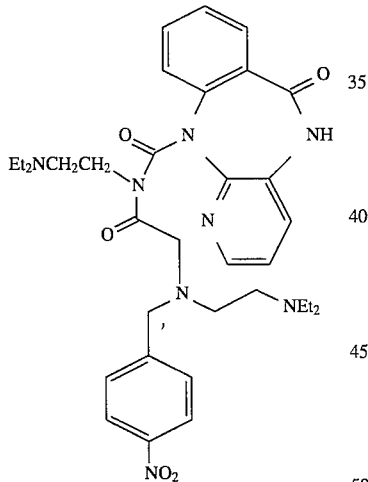

A solution of PDC032. 015 (1.5 grams, 5.6 mmol) and the chloride (1.02 grams, 3.53 mmol) in acetonitrile were refluxed for 20 hours and the reaction was quenched in water. The solvent was removed in vacuo. The product was purified by preparatory TLC (3 purifications) (1:9:90 NH₄OH/MeOH/CHCl₃). The product was extracted from the silica gel with methanol. The methanol was removed in vacuo to yield an amber solid (0.0662 grams). The product was approximately 95% pure by ¹H NMR (CDCl₃).

Preparation of PDC014.030

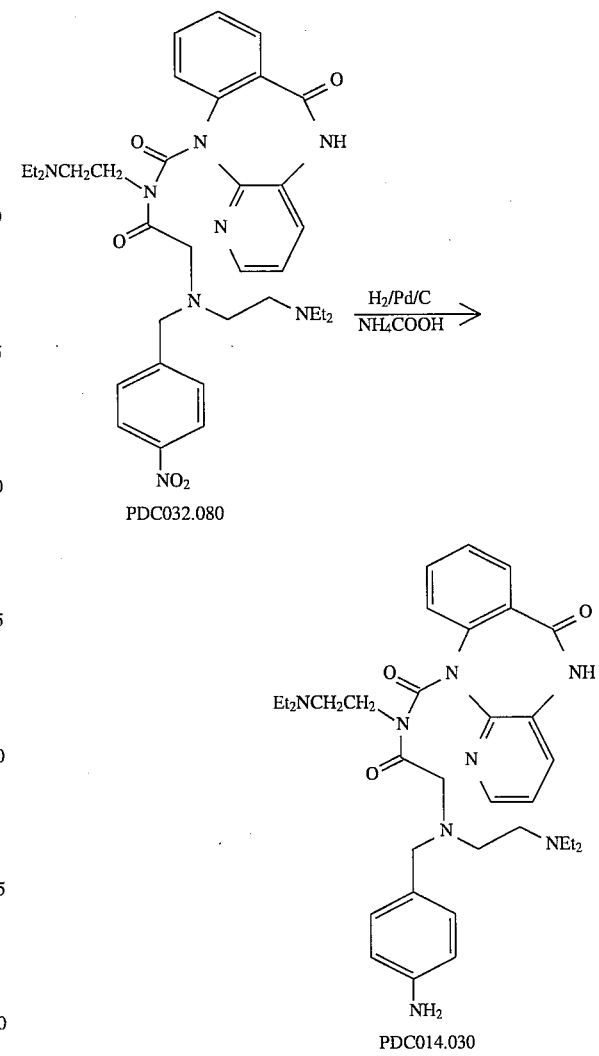

A mixture of PDC032.080 (0.0662 grams, 2 mmol), ammonium bicarbonate (2.7382 grams, 2 mmol), and Pd/C (0.02 grams) in methanol (5 mL) was stirred at room temperature for 1 hour, and the reaction was quenched by adding water. The aqueous phase was basified with aqueous ammonium hydroxide and extracted with chloroform (3×100 mL). The combined organics were evaporated down to an amber colored oil (0.0338 grams).

Preparation of PDC014.034

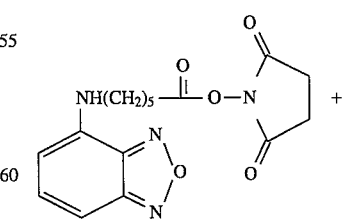

+

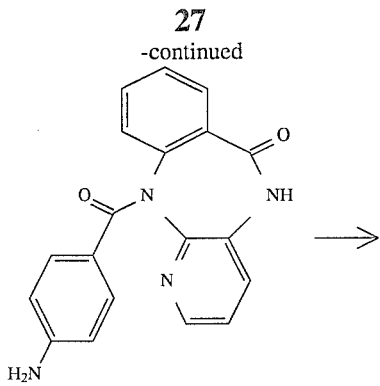

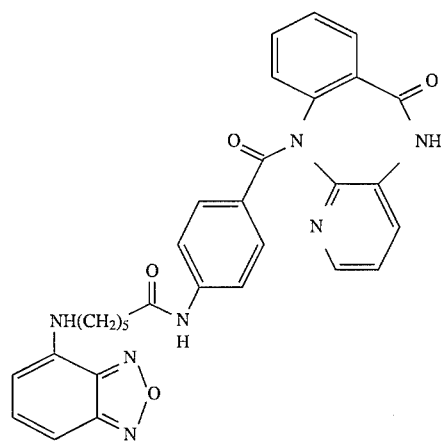

A solution of 6-(7-nitrobenz-2-oxa-1,3-diazo-1,4-yl)amino hexanoate (14.0 mg, 0.0358 mmol) in dimethyl formamide (DMF) (1 mL) was added dropwise to a solution of PDC014-030 (33.8 mg, 0.0715 mmol) in DMF (1 mL). The solution was stirred at room temperature over a weekend. The DMF was removed under high vacuum, and the residue was dissolved in chloroform. The product was purified by preparatory TLC (1:9:90 NH$_4$OH/MeOH/CHCl$_3$). The product was extracted from the silica gel with methanol containing a small amount of ammonia and the methanol was removed in vacuo. The residue was dissolved in absolute ethanol, dried over sodium sulfate, and the solvent removed in vacuo to yield PDC014.034 (0.0216 grams) as an amber solid.

EXAMPLE 9

Synthesis of an N-methyl D-Aspartate receptor fluorescent probe (PDC014.041)

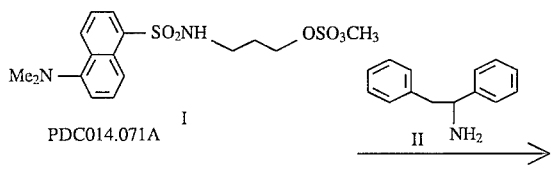

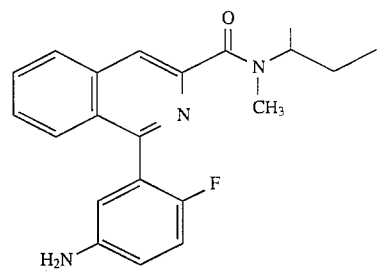

A solution of mesylate I (0.120 grams, 0.3 mmol) and amine II (0.1225 grams, 0.62 mmol, 2 equivalents) in DMF (5 mL) was heated to 50° C and stirred overnight. The DMF was removed in vacuo to give an oil. This oil was purified by preparatory TLC (1:9:90 NH$_4$OH/MeOH/CHCl$_3$) to give PDC014.041 as a yellow solid (0.0093 grams).

EXAMPLE 10

Synthesis of a peripheral benzodiazepine receptor fluorescent probe (PDC018.091)

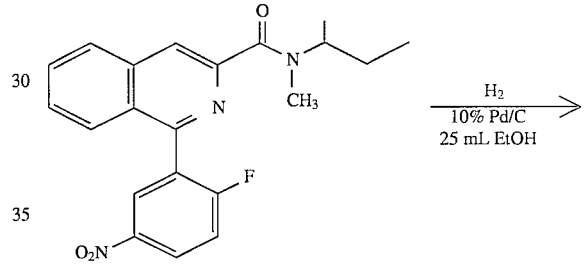

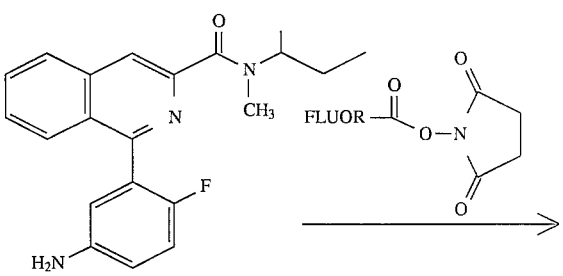

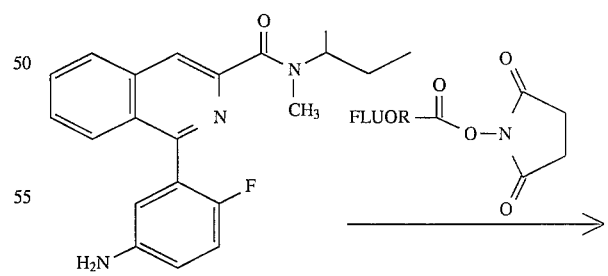

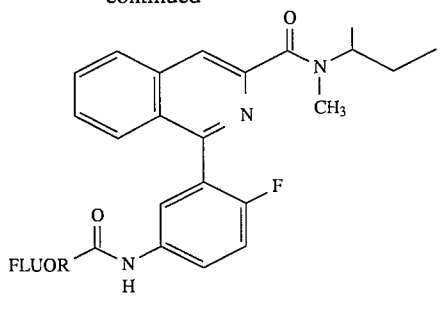

Wherein FLUOR is fluorescein

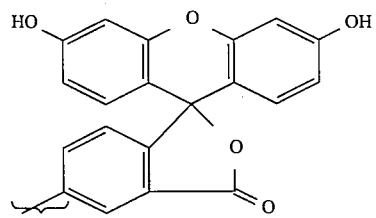

A solution of the nitro aromatic compound (380 mg, 1 mmol) in ethanol (25 mL) was reacted with 10% Pd/C (50 μg) under $H_2$ (50 p.s.i.g) for 45 minutes. TLC (1:5:95 $NH_4OH$/MeOH/chloroform) indicated complete reaction. The resulting aniline compound (240 mg) was isolated by flash chromatography and the NMR of the compound matched the NMR data in the literature reference (McCabe, et al., *J. Pharm. Exper. Ther.*, 262:734–740 (1992).

The aniline (40 mg) was dissolved in DMF (1.0 mL) and 45 mg 5-carboxyfluorescein-N-hydroxysuccinimide (0.1 mmol) and triethylamine (40 μL, 0.3 mmol) were added. The reaction mixture was stirred at room temperature overnight. The product was isolated by preparatory TLC (70:28:2 chloroform/MeOH/$NH_4OH$) to give PDC018.091 (44 mg) as an orange powder.

EXAMPLE 11

Synthesis of sodium channel flourescent probes—Procainamide coupled to an NBD derivative (PDC014.071b)

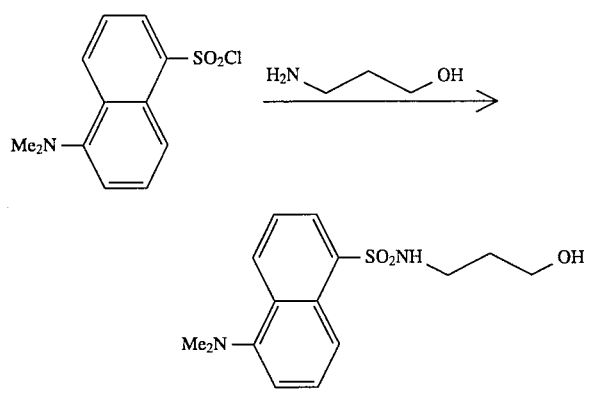

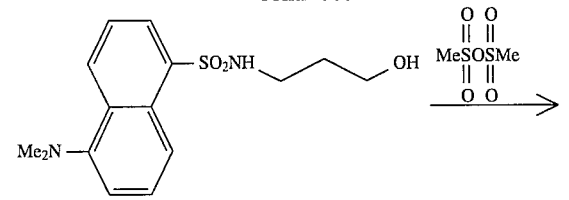

PDC014.071A

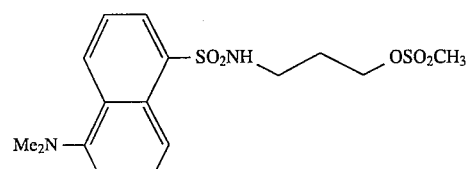

PDC014.071A

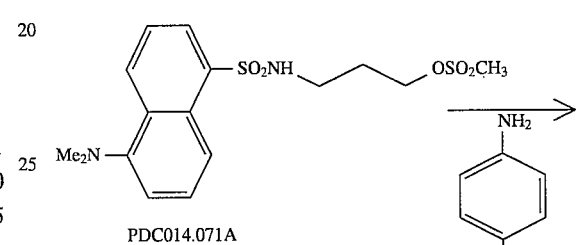

PDC014.071A

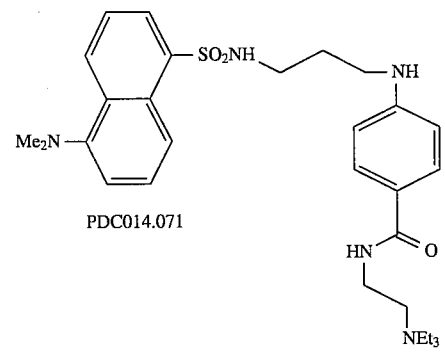

PDC014.071

A solution of dansyl chloride (5.00 grams, 0.185 mol) and 3-amino-propanol (2.99 grams, 0.0371 mmol, 2 equivalents) in methanol (5 mL) was stirred at room temperature for 1 hour, and the reaction was quenched by adding water. The aqueous phase was basified with aqueous ammonium hydroxide and extracted with chloroform. The combined organics were evaporated down to an amber colored oil (PDC014.071a) (5.87 grams).

The resulting dansylated aminopropanol (PDC014.071a) (2 grams, 0.0072 mol) and methane sulfonic anhydride (2.52 grams, 0.01447 mmol, 2 equivalents) were dissolved in pyridine (20 mL) and stirred at room temperature overnight. The pyridine was removed in vacuo and the crude material was used directly in the next step.

The mesylate (0.15 grams, 0.39 mmol), procainamide (0.1824 grams, 0.78 mmol) and potassium iodide (0.5 grams) were added to acetonitrile (15 mL) and the resulting solution was stirred at room temperature over a weekend.

Two products were seen by TLC, and were isolated in crude form by preparative TLC (1:9:90 NH₄OH/MeOH/CHCl₃). 0.0064 grams of the second compound (PDC014.071) were isolated.
EXAMPLE 12
Synthesis of adenosine-A2a receptor fluorescent probes (RDC018.075)
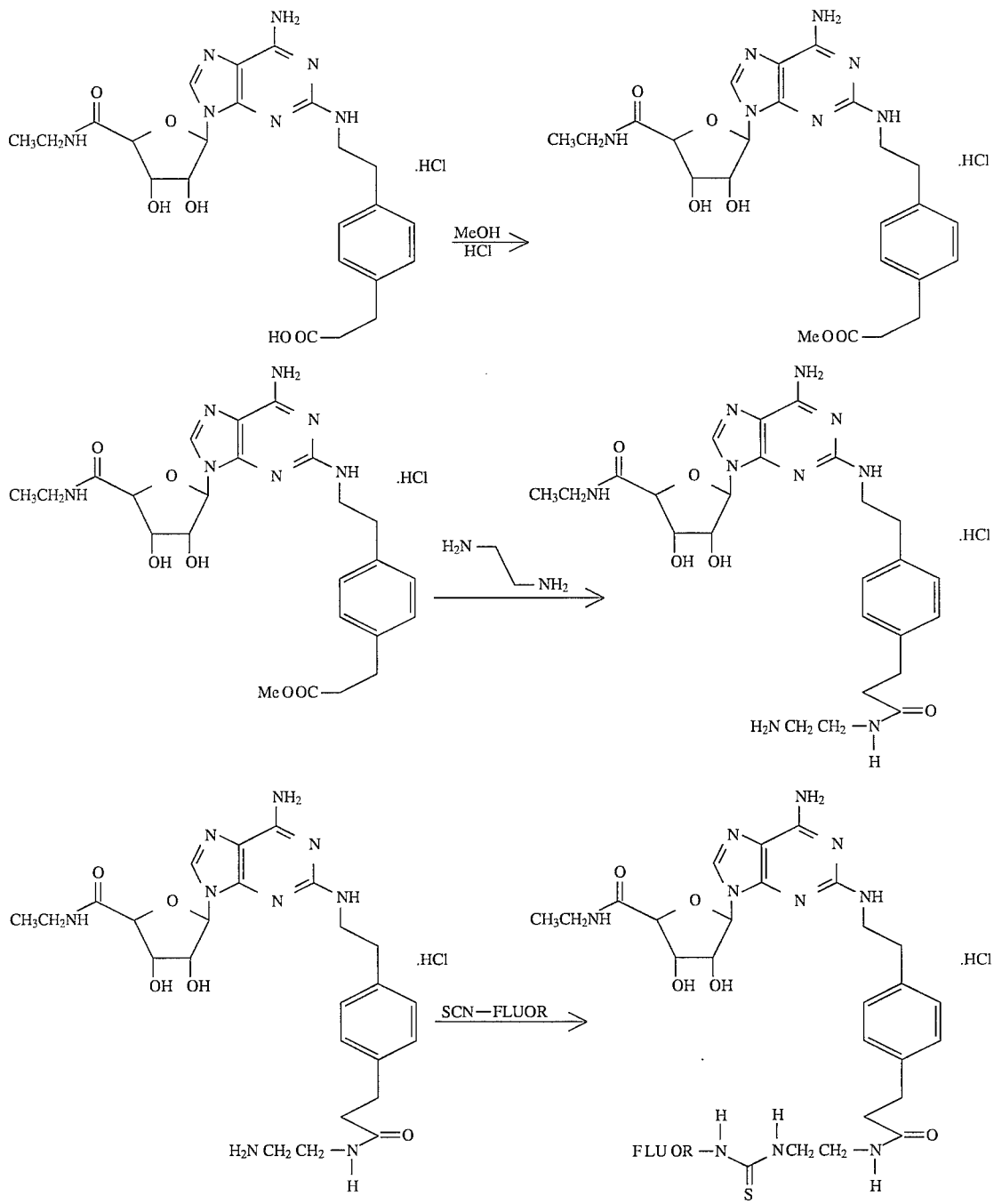

Wherein FLUOR is fluorescein

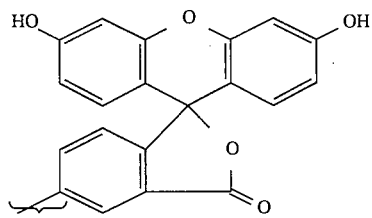

The carboxylic acid (0.2 grams, 0.36 mmol) was dissolved in methanol (10 mL) with heating and HCl (Conc.) (40 μL) was added. The mixture was stirred for 1 hour, and TLC (1/9/15 (NH$_4$OH/MeOH/CHCl$_3$) showed that the reaction was complete. Workup provided the ester (0.180 mg, 97%).

The ester (90 mg, 0.17 mmol) was dissolved in ethylene diamine (5 mL) and heated to 50° C. overnight. The ethylene diamine was removed in vacuo to yield an oily solution. Dropwise addition of ether yielded a yellow oil. Preparatory TLC (1/9/15 (NH$_4$OH/MeOH/CHCl$_3$) afforded the amide (92.1 mg, quantitative yield).

The FLUOR-isocyanate was added to a solution of the amide (92.1 mg, 0.17 mmol) in acetonitrile (5 mL) and isopropanol (5 mL). The reaction mixture was stirred for 24 hours at room temperature. The solvent was removed in vacuo until a solid precipitate began to form, and the solid was precipitated by dropwise addition of a 1:1 mixture of acetonitrile/diethyl ether. The crude solid was filtered and washed with ether. The product was purified by preparatory TLC (70:25:5, chloroform:methanol:NH$_4$OH) and preparatory HPLC (C-4 column, ethyl acetate/water, each with 1% trifluoroacetic acid) to give PDC060.031 (12.5 mg) as a solid.

EXAMPLE 13

Recommended Assay Conditions for ADENOSINE-A$_{2A}$ RECEPTOR LIGAND (PDC 018.075)
Incubation buffer: 50 mM Tris-HCL containing 10mM MgCl$_2$, (pH 7.4 at 25° C.)
Spectra: 492 nm (ex) and 516 nm (em)
Binding Protocol: Binding assays are performed in a 1 ml total volume according to the following conditions:

1. Reconstitution: 10.0 ml of incubation buffer
2. Incubation: 800 μl tissue suspension (300 μg protein/tube) containing adenosine deaminase, 20 μg/mg original tissue weight from calf intestine, fraction IV); 100 μl PDC 018,075; 100 μl buffer or unlabeled ligand (10 μM 2-choroadenosine)
3. Incubation Time: 90 minutes at 25° C.
4. Centrifugation: 20,000×g at 4° C. for 10 minutes and wash with 2×500 μl aliquots of buffer; resuspend pellets in buffer (pH 8.1 at 4° C.); transfer to cuvettes and measure fluorescence intensity
Reference: McCabe et al., *J. Fluorescence*, 1992

EXAMPLE 14

GLYCINE RECEPTOR LIGAND (strychnine-insensitive) (fluorescence quenching compound) (PDC 002.083)
Recommended Assay Conditions:
Incubation buffer: 50 mM HEPES/KOH (pH 8.0 at 4° C.)
Spectra: 486 nm (ex) and 542 nm (em)
Binding Protocol: Binding assays are performed in a 1 ml total volume according to the following conditions:

1. Reconstitution: 10.0 ml of incubation buffer
2. Incubation: 800 μl tissue suspension (200–300 μg protein/tube); 100 μl PDC 002.083; 100 μl buffer or unlabeled ligand (10 μM glycine or d-serine)
3. Incubation Time: 60 minutes at 4° C.
4. Centrifugation: 20,000×g at 4° C. for 10 minutes and wash with 2×500 μl aliquots of buffer; resuspend pellets in buffer; transfer to cuvettes and measure fluorescence intensity

EXAMPLE 15

MUSCARINIC-M$_2$ RECEPTOR LIGAND (PDC 014.034)
Recommended Assay Conditions:
Incubation buffer: 20 mM Hepes, 10 mM Mgcl$_2$ 100 mM NaCl (pH 7.24 at 25° C.)
Spectra: 488 nm (ex) and 549 nm (em)
Binding Protocol: Binding assays are performed in a 1 ml total volume according to the following conditions:

1. Reconstitution: 10.0 ml of incubation buffer
2. Incubation: 800 μl tissue suspension (300 μg protein/tube); 100 μl PDC 014.034; 100 μl buffer or unlabeled ligand (10 μM atropine)
3. Incubation Time: 60 minutes at 25° C.
4. Centrifugation: 20,000×g at 4° C. for 10 minutes and wash with 2×500 μl aliquots of buffer; resuspend pellets in buffer; transfer to cuvettes and measure fluorescence intensity

EXAMPLE 16

NMDA RECEPTOR COMPLEX LIGAND (spectral shift compound) (PDC 014.041)
Recommended Assay Conditions:
Incubation buffer: 5 mM Hepes/Tris (pH 7.8 at 25° C.)
Spectra: 335 nm (ex) and 515 nm (em)
Binding Protocol: Binding assays are performed in a 1 ml total volume according to the following conditions:

1. Reconstitution: 10.0 ml of incubation buffer
2. Incubation: 800 μl tissue suspension (200–300 μg protein/tube); 100 μl PDC 014.041; 100 μl buffer or unlabeled ligand (10 μM (+)mk 801)
3. Incubation Time: 2 hours at 25° C.
4. Measure fluorescence intensity: 335 nm (ex) and 565 nm (em)

EXAMPLE 17

CANNABINOID RECEPTOR LIGAND (PDC 014.063)
Recommended Assay Conditions:
Incubation buffer: 50 mM Tris-Hcl, 3 mM MgCl$_2$, 1 mM EDTA (pH 7.4 at 30° C.)
Spectra: 420 nm (ex) and 520 nm (em)
Binding Protocol: Binding assays are performed in a 1 ml total volume according to the following conditions:

1. Reconstitution: 10.0 ml of incubation buffer
2. Incubation: 800 μl tissue suspension (10 μg protein/tube); 100 μl PDC 014.063; 100 μl buffer or unlabeled ligand (10 anandamide)
3. Incubation Time: 90 minutes at 30° C.
4. Centrifugation: 20,000×g at 4° C. for 10 minutes and wash with 2×500 μl aliquots of buffer; resuspend pellets in buffer (pH 7.4 at 4° C.); transfer to cuvettes and measure fluorescence intensity

EXAMPLE 18

SODIUM CHANNEL MODULATOR (PDC 014.071)
Recommended Assay Conditions:
  incubation buffer:
  Spectra: 335 nm (ex) and 578 nm (em)
  Binding Protocol: Binding assays are performed in a 1 ml total volume according to the following conditions:
  1. Reconstitution: 10.0 ml of incubation buffer
  2. Incubation: 980 µl tissue suspension (µg protein/tube); 10 µl PDC 014.071; 10 µl buffer or unlabeled ligand (10 µM
  3. Incubation Time:
  4. Centrifugation: 20,000×g at 4° C. for 10 minutes and wash with 2×500 µl aliquots of buffer; resuspend pellets in buffer (pH at 4° C.) and measure fluorescence intensity

EXAMPLE 19

MUSCARINIC-$M_1$ RECEPTOR LIGAND (PDC 018.039)
Recommended Assay Conditions:
  Incubation buffer: 20 mM Hepes, 10 mM $MgCl_2$, 100 mM NaCL (pH 7.4 at 25° C.)
  Spectra: 470 nm (ex) and 530 nm (em)
  Binding Protocol: Binding assays are performed in a 1 ml total volume according to the following conditions:
  1. Reconstitution: 10.0 ml of incubation buffer
  2. Incubation: 800 µl tissue suspension (200 µg protein/tube); 100 µl PDC 018.039; 100 µl buffer or unlabeled ligand (1 µM atropine)
  3. Incubation Time: 60 minutes at 4° C.
  4. Centrifugation: 200,000×g at 4° C. for 10 minutes and wash with 2×500 µl aliquots of buffer; resuspend pellets in buffer; transfer to cuvettes and measure fluorescence intensity

EXAMPLE 20

POTASSIUM CHANNEL LIGAND (PDC 018.066)
Recommended Assay Conditions:
  Incubation buffer: 20 mM Hepes (pH at 7.4 at 4° C.)
  Spectra: 330 nm (ex) and 528 nm (em)
  Binding Protocol: Binding assays are performed in a 1 ml total volume according to the following conditions:
  1. Reconstitution: 10.0 ml of incubation buffer
  2. Incubation: 800 µl tissue suspension (200–300 µg protein/tube); 100 µl PDC 018.066; 100 µl buffer or unlabeled ligand (10 µM glyburide)
  3. Incubation Time: 60 minutes at 4° C.
  4. Centrifugation: 20,000×g at 4° C. for 10 minutes and wash with 2×500 µl aliquots of buffer; resuspend pellets in buffer; transfer to cuvettes and measure fluorescence intensity

EXAMPLE 21

$KAPPA_1$ RECEPTOR LIGAND (PDC 018.083)
Recommended Assay Conditions:
  Incubation buffer: 50 mM Tris/HCl, 30 mM $MgCl_2$ (pH 7.4 at 4° C.)
  Spectra: 500 nm (ex) and 522 nm (em)
  Binding Protocol: Binding assays are performed in a 1 ml total volume according to the following conditions:
  1. Reconstitution: 10.0 ml of incubation buffer
  2. Incubation: 800 µl tissue suspension (300 µg protein/tube); 100 µl PDC 018.083; 10 µl buffer or unlabeled ligand (100 µM (−) U50-488)
  3. Incubation Time: 60 minutes at 4° C.
  4. Centrifugation: 20,000×g at 4° C. for 10 minutes and wash with 2×500 µl aliquots of buffer; resuspend pellets in buffer; transfer to cuvettes and measures fluorescence intensity

EXAMPLE 22

PERIPHERAL BENZODIAZEPINE RECEPTOR LIGAND (PDC 018.091)
Recommended Assay Conditions:
  Incubation buffer: 50 Nm Tris-Citrate containing 10 nM $MgCL_2$ (pH 7.0 at 4° C.)
  Spectra: 492 nm (ex) and 516 nm (em)
  Binding Protocol: Binding assays are performed in a 1 ml total volume according to the following conditions:
  1. Reconstitution: 10.0 ml of incubation buffer
  2. Incubation: 800 µl tissue (300 µg protein/tube); 100 µl PDC 018.091; 100 µl buffer or unlabeled ligand (10 µM PK 14105)
  3. Incubation Time: 60 minutes at 4° C.
  4. Centrifugation: 20,000×g at 4° C. for 20 minutes and wash with 2×1 ml aliquots of buffer; resuspend pellets in buffer (pH 8.1 at 4° C.); transfer to cuvettes and measure fluorescence intensity
  Reference: McCabe et al., JPET, 262:734–740, 1992
  AQ-RA 741, MK 801, U50,488, PK 14105, and CGS 21680 are publicly available, and may be obtained from, e.g., Research Biochemicals Inc. (Natick, Mass.), and other sources.

Modifications and variations of the method and compositions of the present invention will be obvious to those skilled in the art from the foregoing detailed description of the invention. Such modifications and variations are intended to come within the scope of the following claims.

We claim:

1. A fluorescent conjugate comprising
   a ligand selected from the group consisting of compounds specifically and selectively binding to N-methyl-D-aspartate, cannabinoid, glycine, sodium channel, and potassium channel receptors, and
   a fluorescent label bound to the ligand,
   wherein the labeled ligand binds specifically to a receptor with an affinity of less than or equal to one micromolar and the label is directly detectable in the visible spectrum.

2. The conjugate of claim 1 wherein the affinity of the labeled ligand is less than or equal to 100 nanomolar.

3. The conjugate of claim 1 wherein the label is selected from the group consisting of fluorescein, fluorescent derivatives of fluorescein, Texas red, nitrobenz-2-oxa-1,3-diazol-4-yl (NBD), coumarin, dansyl chloride, rhodamine and fluorescent derivatives of rhodamine.

4. The conjugate of claim 1 wherein the ligand and the label are linked by a spacer.

5. The conjugate of claim 1 wherein the ligand is derived from anandamide and specifically binds to cannabinoid receptors, and the fluorescent label is derived from nitrobenz-2-oxa-1,3-diazol-4-yl.

6. The conjugate of claim 1 wherein the ligand is derived from anandamide and specifically binds to cannabinoid receptors, and the fluorescent label is derived from dansyl chloride.

7. The conjugate of claim 1 wherein the ligand is derived from dichlorokynurenic acid and specifically binds to glycine receptors, and the fluorescent label is derived from nitrobenz-2-oxa-1,3-diazol-4-yl.

8. The conjugate of claim 1 wherein the ligand is derived from MK 801 and specifically binds to N-methyl-D-aspartate receptors, and the fluorescent label is derived from dansyl chloride.

9. The conjugate of claim 1 wherein the ligand is derived from glibenclamide and specifically binds to potassium channel receptors, and the fluorescent label is derived from nitrobenz-2-oxa-1,3-diazol-4-yl.

10. The conjugate of claim 1 wherein the ligand is derived from procainamide and specifically binds to sodium channel receptors, and the fluorescent label is derived from dansyl chloride.

* * * * *